US009687559B2

(12) United States Patent
DeAngelis

(10) Patent No.: US 9,687,559 B2
(45) Date of Patent: *Jun. 27, 2017

(54) HEPAROSAN POLYMERS AND METHODS OF MAKING AND USING SAME FOR THE ENHANCEMENT OF THERAPEUTICS

(75) Inventor: Paul L. DeAngelis, Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 810 days.

This patent is subject to a terminal disclaimer.

(21) Appl. No.: 12/556,324

(22) Filed: Sep. 9, 2009

(65) Prior Publication Data

US 2010/0036001 A1 Feb. 11, 2010

Related U.S. Application Data

(63) Continuation-in-part of application No. 12/383,046, filed on Mar. 19, 2009, now abandoned.

(60) Provisional application No. 61/179,275, filed on May 18, 2009, provisional application No. 61/038,027, filed on Mar. 19, 2008, provisional application No. 61/095,572, filed on Sep. 9, 2008.

(51) Int. Cl.
*A61K 31/70* (2006.01)
*A61K 31/727* (2006.01)
*A61K 47/48* (2006.01)

(52) U.S. Cl.
CPC ................................ *A61K 47/4823* (2013.01)

(58) Field of Classification Search
None
See application file for complete search history.

(56) References Cited

U.S. PATENT DOCUMENTS

| | | | |
|---|---|---|---|
| 5,314,876 A | 5/1994 | Lormeau et al. | |
| 5,384,398 A | 1/1995 | Lormeau et al. | |
| 5,470,911 A | 11/1995 | Rhee et al. | |
| 5,550,187 A | 8/1996 | Rhee et al. | |
| 5,756,553 A | 5/1998 | Iguchi et al. | |
| 5,827,937 A | 10/1998 | Ågerup | |
| 5,876,433 A | 3/1999 | Lunn | |
| 5,958,899 A | 9/1999 | Zoppetti et al. | |
| 6,120,536 A | 9/2000 | Ding et al. | |
| 6,156,373 A | 12/2000 | Zhong et al. | |
| 6,162,797 A | 12/2000 | Zoppetti et al. | |
| 6,444,447 B1 | 9/2002 | DeAngelis | |
| 6,562,781 B1 | 5/2003 | Berry et al. | |
| 7,244,270 B2 | 7/2007 | Lesh | |
| 7,291,673 B2 | 11/2007 | Hubbell et al. | |
| 7,842,500 B2 * | 11/2010 | Suzuki | C07K 16/44 435/252.33 |
| 8,580,290 B2 | 11/2013 | DeAngelis | |
| 8,980,608 B2 | 3/2015 | DeAngelis et al. | |
| 2002/0192205 A1 | 12/2002 | Michon et al. | |
| 2002/0193516 A1 | 12/2002 | Bucevschi et al. | |
| 2003/0017131 A1 | 1/2003 | Park et al. | |
| 2004/0087488 A1 * | 5/2004 | Parent et al. | 514/2 |
| 2004/0132143 A1 * | 7/2004 | DeAngelis et al. | 435/89 |
| 2004/0197868 A1 | 10/2004 | DeAngelis | |
| 2005/0255562 A1 | 11/2005 | Rosenberg et al. | |
| 2005/0272696 A1 * | 12/2005 | DeAngelis | 514/54 |
| 2006/0105431 A1 | 5/2006 | DeAngelis | |
| 2006/0116346 A1 | 6/2006 | De Luca et al. | |
| 2006/0172967 A1 | 8/2006 | Toida | |
| 2006/0188966 A1 | 8/2006 | DeAngelis | |
| 2007/0128703 A1 * | 6/2007 | DeAngelis et al. | 435/85 |
| 2008/0109236 A1 | 5/2008 | DeAngelis et al. | |
| 2008/0112951 A1 | 5/2008 | Phalipon et al. | |
| 2008/0226690 A1 | 9/2008 | DeAngelis | |
| 2009/0104627 A1 * | 4/2009 | Yamamoto et al. | 435/7.4 |
| 2012/0108802 A1 | 5/2012 | DeAngelis et al. | |
| 2015/0118185 A1 | 4/2015 | DeAngelis | |

FOREIGN PATENT DOCUMENTS

| | | | |
|---|---|---|---|
| EP | 1870421 A1 | 12/2007 | |
| EP | 1923402 A1 | 5/2008 | |
| JP | 2004018840 | 1/2004 | |
| JP | WO2007/001021 | * | 1/2007 |
| WO | 9222331 A1 | 12/1992 | |
| WO | 9741897 A1 | 11/1997 | |
| WO | WO 00/27437 | 5/2000 | |
| WO | WO 02/89742 A2 | 5/2002 | |
| WO | WO 03/029261 A2 | 10/2003 | |
| WO | WO 2009014559 | 1/2009 | |
| WO | WO 2010030342 | 3/2010 | |

OTHER PUBLICATIONS

Remington, The Science and Practice of Pharmacy, Nineteenth Edition-1995, pp. 1463, 1546-1547.*
Remington, The Science and Practice of Pharmacy, Nineteenth Edition-1995, pp. 710-712.*
May, B.J. et al. Complete genomic sequence of Pasteurella multocida, Pm70. Proc. Natl. Acad. Sci. (USA) Mar. 2001, vol. 98. No. 6, pp. 3460-3465.
Townsend, K.M. et al. Genetic organization of Pasteurella multocida cap loci and development of a multiplex capsular typing system. J. Clin. Microbiol. Mar. 2001. vol. 39. No. 3, pp. 924-929.
Hill, A.L., et al.: Identification of the *Xenopus laevis* cDNA for EXT1: A Phylogenetic Perspective. DNA Sequence, 2002 vol. 13 (2), pp. 85-92; ISSN: 10472-5179; Taylor & Francis, Ltd. (USA).
Rimler, R.B.: Presumptive Identification of *Pasteurella multocida serogroups* A, D and F by capsule depolymerisation with mucopolysaccharidases. Veterinary Record (1994) 134, 191-192 (USA).
Poggi A., et al.: Inhibition of B16-BL6 melanoma lung colonies by semisynthetic sulfaminoheparosan sulfates from *E. coli* K5 polysaccharide. Semin Thromb Hemost. Aug. 2002; 28(4): 383-92. vol. 28, No. 4.
Kim, B.T., et al.: Human tumor suppressor EXT gene family members EXTL1 and EXTL3 encode alpha 1,4-N-acetylglucosaminyltransferases that likely are involved in heparan sulfate/heparin biosynthesis. Proc. Natl. Acad. Sci. U.S.A. 2001 Jun. 19, 1998 (13):7176-81.

(Continued)

*Primary Examiner* — Shobha Kantamneni
(74) *Attorney, Agent, or Firm* — Dunlap Codding, P.C.

(57) ABSTRACT

The present invention includes compositions, methods, and systems for the development and use of heparosan, a natural polymer related to heparin, as a new therapeutic modifying agent or vehicle which can modulate drug cargo pharmacokinetics and behavior within a mammalian patient.

31 Claims, 10 Drawing Sheets

(56) References Cited

OTHER PUBLICATIONS

Vicenzi, E., et al.: Broad spectrum inhibition of HIV-1 infection by sulfated K5 *Escherichia coli* polysaccharide derivatives. AIDS. Jan. 24, 2003; 17 (2): 177-81; ISSN: 0269-9370 Lippincott Williams & Wilkins; Italy.

Lin, X, et al.: Expression and functional analysis of mouse EXT1, a homolog exostoses type 1 gene. Biochem Biophys Res Commun. Jul. 30, 1998; 248(3): 738-43; Academic Press.

Legeai-Mallet L., et al.: EXT 1 Gene Mutation Induces Chondrocyte Cytoskeletal Abnormalities and Defective Collagen Expression in the Exostoses. J Bone Miner Res. Aug. 2000; 15(8):1489-500.

McCormick, C., et al.: The putative tumor suppressor EXT1 alters the expression of cell-surface heparan sulfate. Nat. Genet. Jun. 1998; 19(2):158-61. (Canada).

Ahn, J., et al.: Cloning of the putative tumor suppressor gene for hereditary multiple exostoses (EXT1). Nat. Genet. Oct. 1995; 11(2):137-43.

Stickens, D., et al.: The EXT2 multiple exostoses gene defines a family of putative tumor suppressor genes. Nat. Genet. Sep. 1996; 14(1):25-32.

Simmons, A.D., et al.: A direct interaction between EXT proteins and glycosyltransferases is defective in hereditary multple exostoses. Hum. Mol. Genet. Nov. 1999; 8(12):2155-64 (USA).

Hagner-McWhirter A., et al.: Biosynthesis of heparin/heparan sulfate: kinetic studies of the glucuronyl C5-epimerase with N-sulfated derivatives of the *Escherichia coli* K5 capsular polysaccharide as substrates. Glycobiology. Feb. 2000; 10(2):159-71. Oxford University Press. (USA).

Lidholt, K., et al.: Biosynthesis of heparin. The D-glucuronosyl- and N-acetyl-D-glucosaminyltransferase reactions and their relation to polymer modification. Biochem J. Oct. 1, 1992;287 (pt 1):21-9 (Sweden).

Lin, X., et al.: Disruption of gastrulation and heparan sulfate biosynthesis in EXT1-Deficient Mice. Dev. Biol. Aug. 15, 2000; 224(2):299-311. Academic Press. (USA).

Van Hul, W., et al.: Identification of a Third EXT-like Gene (EXTL3) Belonging to the EXT Gene Family; Genomics. Jan. 15, 1998;47(2):230-7. Academic Press. (Belgium).

Nader, H.B., et al.: New insights on the specificity of heparin and haparan sulfate lyases from Flavobacterium heparinum revealed by the use of synthetic derivatives of K5 polysaccharide from *E. coli* and 2-O-desulfated heparin. Glycoconj J. Jun. 1999; 16(6):265-70. Kluwer Academic Publishers. Manufactured in the Netherlands. (Brazil).

DeAngelis, P.L., et al.: Identification and Molecular Cloning of a Heparosan Synthase from Pasteurella multocida Type D. The Journal of Biological Chemistry. vol. 277, No. 9, ISSN: Mar. 1, pp. 7209-7213, 2002. (USA).

Naggi, A., et al.: Toward a Biotechnological Heparin through Combined Chemical and Enzymatic Modification of the *Escherichia coli* K5 Polysaccharide. Seminars in Thrombosis and Hemostasis, vol. 27, No. 5, 2001; pp. 437-443. (Italy).

Leali, D., et al.: Fibroblast Growth Factor-2 Antagonist Activity and Angiostatic Capacity of Sulfated *Escherichia coli* K5 Polysaccharide Derivatives. The Journal of Biological Chemistry, vol. 276, No. 41. ISSN: Oct. 12, pp. 37900-37908, 2001. (Italy).

Duncan, G., et al.: The link between heparan sulfate and hereditary bone disease: finding a function for the EXT family of putative tumor suppressor proteins. The Journal of Clinical Investigation, Aug. 2001, vol. 108, No. 4, pp. 511-516. (USA).

Kim, B-T, et al.: Demonstration of a Novel Gene DEXT3 of *Drosophila melanogaster* as the Essential N-Acetylglucosamine Transferase in the Heparan Sulfate Biosynthesis. The Journal of Biological Chemistry, vol. 277, No. 16, ISSN: Apr. 19, pp. 13659-13665, 2002. (Sweden).

Sugahara, K., et al.: Heparin and Heparan Sulfate Biosynthesis. Life, 54:163-175, 2002. (Japan).

Lind, T., et al.: Biosynthesis of Heparin/Heparan Sulfate. The Journal of Biological Chemistry, vol. 268, No. 28, ISSN: Oct. 5, pp. 20705-20708, 1993. (Sweden).

Wei, G., et al.: Location of the Glucuronosyltransferase Domain in the Heparan Sulfate Copolymerase EXT1 by Analysis of Chinese Hamster Ovary Cell Mutants. The Journal of Biological Chemistry, vol. 275, No. 36, ISSN: Sep. 8, pp. 27733-27740, 2000. (USA).

Razi, N., et al.: Structural and functional properties of heparin analogues obtained by chemical sulphation of *Escherichia coli* K5 capsular polysaccharide. Biochem J. Jul. 15, 1995;309 (pt2):465-72. (Sweden).

Kusche, M., et al.: Biosynthesis of heparin. Use of *Escherichia coli* K5 capsular polysaccharide as a model substrate in enzymic polymer-modification reactions. Biochem J. Apr. 1, 1991;275 (pt1): 151-8. (Sweden).

Casu, B., et al.: Heparin-like compounds prepared by chemical modification of capsular polysaccharide from *E. coli*. Elsevier Science 1994; pp. 271-284. (Italy).

Vann, W.F., et al.: The Structure of the Capsular Polysaccharide (K5 Antigen) of Urinary-Tract-Infective *Escherichia coli* 010:K5:H4. Biochem J. 1981; 116; pp. 359-364. (Germany).

Toyoda, H., et al.: Structural Analysis of Glycosaminoglycans in *Drosophila* and *Caenorhabditis elegans* and Demonstrations That *tout-velu*, a *Drosophila* Gene Related to EXT Tumor Suppressors, Affects Heparan Sulfate in Vivo. The Journal of Biological Chemistry, vol. 275, No. 4; ISSN: Jan. 28, pp. 2269-2275, 2000. (Japan).

Zak, B.M., et al.: Hereditary multiple exostoses and heparan sulfate polymerization. Biochimica et Biophysica Acta 1573 (2002) 346-355. (USA).

Katada, T., et al.: cDNA cloning and distribution of XEXT1, the *Xenopus* homologue of EXT1. Dev Genese Evol. (2002) 212:248-250. (Japan).

Kitagawa, H., et al.: The Tumor Suppressor EXT-like Gene EXTL2 Encodes an 1, 4-N-Acetylhexosaminylatransferase That Transfers N-Acetylgalactosamine and N-Acetylglucosamine to the Common Clycosaminoglycan-Protein Linkage Region. The Journal of Biological Chemistry. 263(20):13933-139337.

Kitagawa, H., et al.: rib-2, a *Caenorhabditis elegans* Homolog of the Human Tumor Suppressor EXT Genes Encodes a Novel 1,4-N-Acetylglucosaminyltransferase Involved in the Biosynthetic Initiation and Elongation of Heparan Sulfate. The Journal of Biological Chemistry, vol. 276, No. 7; ISSN: Feb. 16, pp. 4834-4838, 2001. (Japan).

Song, G., et al.: Identification of mutations in the human EXT1 and EXT2 genes. Chin J. Med. Genet., Aug. 1999, vol. 16. No. 4, pp. 208-210. (China).

Clines, G.A., et al.: The Structure of the Human Multiple *Exostoses* 2 Gene and Characterization of Homologs in Mouse and *Caenorhabditis elegans*. Cold Spring Harbor Laboratory Press 1997; ISSN: 1057-9803, pp. 359-367. (USA).

Wise, C.A., et al.: Identification and Localization of the Gene for EXTL, a Third Member of the Multiple Exostoses Gene Family. Cold Spring Harbor Laboratory Press 1997; ISSN: 1057-9803, pp. 10-16. (USA).

Linhardt, R.J., et al.: Production and Chemical Processing of Low Molecular Weight Heparins. Thieme Medical Publishers, Inc. 1999, vol. 25, Suppl. 3, pp. 5-16. (USA).

Fareed, J.: Heparin, Its Fractions, Fragments and Derivatives. Some Newer Perspectives. Seminars in Thrombosis and Hemostasis, vol. 11, No. 1, 1985, pp. 1-9.

Lind, T., et al.: The Putative Tumor Suppressors EXT1 and EXT2 Are Glycosyltransferases Required for the Biosynthesis of Heparan Sulfate. The Journal of Biological Chemistry, vol. 273, No. 41, ISSN: Oct. 9, pp. 26265-26268, 1998. (Sweden).

Senay, C., et al.: The EXT1/EXT2 tumor suppressors: catalytic activities and role in heparan sulfate biosynthesis. EMBO Reports vol. 1, No. 3, pp. 282-286, 2000. ((Sweden).

Bio TIE Therapies; BioHeparin—Prospectus; Jun. 2001. (Finland).

Sasisekharan, R., et al.: Heparin and heparan sulfate: biosynthesis, structure and function. Elsevier Science, Ltd. 2000; 1367-5931; pp. 626-631. (USA).

(56) References Cited

OTHER PUBLICATIONS

Pedersen, L.C., et al.: Heparan/Chondroitin Sulfate Biosynthesis. The Journal of Biological Chemistry, vol. 275, No. 44; ISSN: Nov. 3, pp. 34580-34585, 2000. (USA).
Finke, A., et al.: Biosynthesis of the *Escherichia coli* K5 Polysaccharide, a Representative of Group II Polysaccharides: Polymerization In Vitro and Characterization of the Product. Journal of Bacteriology, Jul. 1999, pp. 4088-4094. (Germany).
Griffiths, G., et al.: Characterization of the Glycosyltransferase Enzyme from the *Escherichia coli* K5 Capsule Gene Cluster and Identification and Charaterization of the Glucuronyl Active Site. The Journal of Biological Chemistry, vol. 273, No. 19, ISSN: May 8, pp. 11752-11757, 1998. (United Kingdom).
Hodson, N., et al.: Identification That KfiA, a Protein Essential for the Biosynthesis of the *Escherichia coli* K5 Capsular Polysaccharide, Is a UDP-GlcNAc Glycosyltransferase. The Journal of Biological Chemistry, vol. 275, No. 35, ISSN: Sep. 1, pp. 27311-27315, 2000. (United Kingdom).
Townsend, K.M., et al.: Genetic Organization of *Pasteurella multocida cap* Loci and Development of a Multiplex Capsular PCR Typing System. Journal of Clinical Microbiology, Mar. 2001, pp. 924-929. (Australia).
Boyce, J.D., et al.: *Pasteurella multocida* capsule: composition, function and genetics. Journal of Biotechnology 83 (2000) pp. 153-160. (Australia).
Rimler, R.B., et al.: Influence of chondroitinase on direct hemagglutination titers and phagocytosis of *Pasteurella multocida* serogroups A, D and F. Veterinary Microbiology 47 (1995) pp. 287-294. (USA).
Rigg, G.P., et al.: The localization of KpsC, S and T, and KfiA, C and D Proteins Involved in the biosynthesis of the *Escherichia coli* K5 capsular polysaccharide: evidence for a membrane-bound complex. Microbiology (1998), 144, 2905-2914. (United Kingdom).
DeAngelis, P.L., et al.: Identification of the capsular polysaccharides of Type D and F *Pasteurella multocida* as unmodified heparin and chondroitin, respectively. Carbohydrate Research 337 (2002) pp. 1547-1552. (USA).
Jing, W., et al.: Structure function analysis of *Pasteurella* glycosaminoglycan synthesis. Glycobiology 2002 12: abstract 188. (USA).
McCormick, C., et al.: The putative tumor suppressors EXT1 and EXT2 form a stable complex that accumulates in the Golgi apparatus and catalyzes the synthesis of heparab sulfate. PNAS, Jan. 18, 2000, vol. 97, No. 2, pp. 668-673. (Canada).
Cheung, P.K., et al.: Etiological Point Mutations in the Hereditary Multiple Exostoses Gene EXT1: A Functional Analysis of Heparan Sulfate Polymerase Activity. Am. J. Hum. Genet. 69:55-66, 2001. (Canada).
Wyatt Technology Corporation: Heparin Characterization. Apr. 5, 1997; www.tigc.org.
Soldani, G., et al.: Experimental and Clinical Pharmacology of Glycosaminoglycans (GAGs). Drugs Exptl. Clin. Res. XVII(1) 81-85 (1991). (Italy).
Van Aken, H., et al.: Anticoagulation: The Present and Future. Clin. Appl. Thrombosis/Hemostasis, 7(3): 195-204, 2001. (Germany).
Lidholt, K., et al.: Substrate specificities of glycosyltransferases involved in formation of heparin precursor and *E. coli* K5 capsular polysaccharides. Carbohydrate Research, 255 (1994) 87-101. (Sweden).
Roberts, I., et al.: Molecular Cloning and Analysis of Genes for Production of K5, K7, K12, and K92 Capsular Polysaccharides in *Escherichia coli*. J. Bacteriology; Dec. 1986, pp. 1228-1233. (Germany).
Kroncke, K.D., et al.: Expression of the *Escherichia coli* K5 Capsular Antigen: Immunoelectron Microscopic and Biochemical Studies with Recombinant *E. coli*. J. Bacteriology, Feb. 1990, pp. 1085-1091. (Germany).

Roberts, I.S., et al.: Common Organization of Gene Clusters for Production of Different Capsular Polysaccharides (K Antigens) in *Escherichia coli*. J. Bacteriology, Mar. 1988, pp. 1305-1310. (United Kingdom).
Petit, C., et al.: Region 2 of the *Escherichia coli* K5 capsule gene cluster encoding proteins for the biosynthesis of the K5 polysaccharide. Molecular Microbiology (1995) 17(4), pp. 611-620. (United Kingdom).
Smith, A.N., et al.: Molecular analysis of the *Escherichia coli* K5 *kps* locus: identification and characterization of an inner-membrane capsular polysaccharide transport system. Molecular Microbiology (1990) 4(11), pp. 1863-1869. (United Kingdom).
Bronner, D., et al.: Synthesis of the K5 (group II) capsular polysaccharide in transport-deficient recombinant *Escherichia coli*. FEMS Microbiology Letters 113 (1993), pp. 273-284.
Pandit, K.K., et al.: Capsular hyaluronic acid in Pasteurella multocida type A and its counterpart in type D. Research in Veterinary Science. 54:20-24 (1993).
Linhardt, R.J. et al.; "Isolation and characterization of human heparin". Biochemistry, vol. 31(49): 12441-12445 (1992).
DeAngelis, P.; "Microbial glycosaminoglycan glycosyltransferases". Glysobiology, vol. 12(1): 9R-16R (2002).
Suzuki, et al.; "Generation and characterization of a series of monoclonal antibodies that specifically recognize [HexA(ÃÂ+-2S)-GlcNAc]n epitopes in heparan sulfate"; Glycoconjugate Journal, Kluwer Academic Publishers, BO, May 2008; vol. 25, No. 8; pp. 703-712, XP019642419, ISSN: 1573-4986, DOI: 10.1007/S10719-008-9130-Z.
Sismey-Ragatz, et al.; "Chemoenzymatic Synthesis with Distinct Pasteurella Heparosan Synthases: Monodisperse Polymers and Unnatural Structures"; Journal of Biological Chemistry, Jul. 2007; vol. 282, No. 39; pp. 28321-28327, XP055116675, ISSN: 0021-9258, DOI: 10.1074/jbc.M701599200.
U.S. Appl. No. 14/060,077; Paul L. DeAngelis, Office Action dated Aug. 26, 2015.
English translation of JP20014-018840 above, downloaded from European Patent Office on May 19, 2015.
U.S. Appl. No. 13/325,181; Paul L. DeAngelis; Final Office Action dated May 28, 2015.
PCT Application No. PCT/US02/14581, Paul DeAngelis, International Search Report, dated Jun. 11, 2003.
PCT Application No. PCT/US02/14581, Paul DeAngelis, Written Opinion, dated Aug. 5, 2004.
U.S. Appl. No. 10/142,143, Paul DeAngelis, Requirement for Restriction/Election, dated Mar. 29, 2005.
U.S. Appl. No. 10/142,143, Paul DeAngelis, Response to Election, dated Apr. 29, 2005.
U.S. Appl. No. 10/142,143, Paul DeAngelis, Office Action, dated Oct. 28, 2005.
U.S. Appl. No. 10/142,143, Paul DeAngelis, Response to Office Action, dated Apr. 14, 2006.
U.S. Appl. No. 10/142,143, Paul DeAngelis, Office Action, dated Jun. 22, 2006.
U.S. Appl. No. 10/142,143, Paul DeAngelis, Response to Office Action, dated Dec. 22, 2006.
U.S. Appl. No. 10/142,143, Paul DeAngelis, Final Office Action, dated Apr. 5, 2007.
U.S. Appl. No. 10/142,143, Paul DeAngelis, Amendment Under 37 CRF 1.116, dated Jul. 3, 2007.
Australian Serial No. 2002256501, Paul DeAngelis, Examiner's First Report, dated Nov. 7, 2006.
Australian Serial No. 2002256501, Paul DeAngelis, Response to Examiner's First Report, dated Apr. 24, 2008.
EPO Application No. 02725971.2, Paul DeAngelis, Official Letter, dated Apr. 24, 2006.
EPO Application No. 02725971.2, Paul DeAngelis, Response to Official Letter, Nov. 3, 2006.
EPO Application No. 02725971.2, Paul DeAngelis, Official Letter, dated Mar. 2, 2009.
EPO Application No. 02725971.2, Paul DeAngelis, Response to Official Letter, dated Sep. 1, 2009.
EPO Application No. 02725971.2, Paul DeAngelis, Official Letter, dated Apr. 24, 2012.

(56) References Cited

OTHER PUBLICATIONS

PCT Application No. PCT/US08/04190, Paul DeAngelis, International Search Report & Written Opinion, dated Mar. 24, 2009.
PCT Application No. PCT/US09/05050, Paul DeAngelis, International Search Report & Written Opinion, dated Sep. 9, 2009.
U.S. Appl. No. 10/814,752, Paul DeAngelis, Requirement for Restriction/Election, dated Jul. 25, 2006.
U.S. Appl. No. 10/814,752, Paul DeAngelis, Amendment & Response to Election, dated Jan. 25, 2007.
U.S. Appl. No. 10/814,752, Paul DeAngelis, Office Action, dated Apr. 16, 2007.
U.S. Appl. No. 10/814,752, Paul DeAngelis, Amendment & Response to Office Action, dated Oct. 16, 2007.
U.S. Appl. No. 10/814,752, Paul DeAngelis, Office Action, dated Dec. 27, 2007.
U.S. Appl. No. 10/814,752, Paul DeAngelis, Amendment & Response to Office Action, dated Jun. 24, 2008.
U.S. Appl. No. 10/814,752, Paul DeAngelis, Final Office Action, dated Dec. 4, 2008.
U.S. Appl. No. 11/975,811, Paul DeAngelis, Requirement for Restriction/Election, dated Aug. 26, 2009.
U.S. Appl. No. 11/975,811, Paul DeAngelis, Amendment & Response to Election, dated Sep. 29, 2009.
U.S. Appl. No. 11/975,811, Paul DeAngelis, Office Action, dated Oct. 29, 2009.
U.S. Appl. No. 11/975,811, Paul DeAngelis, Amendment & Response to Office Action, dated Jan. 26, 2010.
U.S. Appl. No. 11/975,811, Paul DeAngelis, Notice of Allowance with Examiner's Amendment, dated Apr. 12, 2010.
U.S. Appl. No. 11/975,811, Paul DeAngelis, Amendment Under 37 CFR 1.312, dated Jun. 8, 2010.
U.S. Appl. No. 11/906,704, Paul DeAngelis, Requirement for Restriction/Election, dated Nov. 18, 2009.
U.S. Appl. No. 11/906,704, Paul DeAngelis, Amendment & Response to Election, dated Dec. 18, 2009.
U.S. Appl. No. 11/906,704, Paul DeAngelis, Requirement for Restriction/Election, dated Feb. 2, 2010.
U.S. Appl. No. 11/906,704, Paul DeAngelis, Amendment & Response to Election, dated Feb. 24, 2010.
U.S. Appl. No. 11/906,704, Paul DeAngelis, Office Action, dated May 17, 2010.
U.S. Appl. No. 11/906,704, Paul DeAngelis, Amendment & Response to Office Action, dated Nov. 17, 2010.
U.S. Appl. No. 11/906,704, Paul DeAngelis, Final Office Action, dated Jan. 18, 2011.
U.S. Appl. No. 11/906,704, Paul DeAngelis, Pre-Appeal Brief Request for Review, dated Jul. 18, 2011.
U.S. Appl. No. 11/906,704, Paul DeAngelis, Notice of Allowance with Examiner's Amendment, dated Aug. 31, 2011.
U.S. Appl. No. 12/080,060, Paul DeAngelis, Requirement for Restriction/Election, dated Nov. 3, 2010.
U.S. Appl. No. 12/080,060, Paul DeAngelis, Amendment & Response to Election, dated Jan. 19, 2011.
U.S. Appl. No. 12/080,060, Paul DeAngelis, Office Action, dated Feb. 2, 2011.
U.S. Appl. No. 12/080,060, Paul DeAngelis, Amendment & Response to Office Action, dated Aug. 1, 2011.
U.S. Appl. No. 12/080,060, Paul DeAngelis, Final Office Action, dated Dec. 29, 2011.
U.S. Appl. No. 12/080,060, Paul DeAngelis, Amendment & Response to Final Office Action, dated Jun. 28, 2012.
Australian Application No. 2008207616, Paul DeAngelis, Examiner's Report, dated Oct. 18, 2010.
Australian Application No. 2008207616, Paul DeAngelis, Response to Examiner's Report, dated Oct. 18, 2011.
Jing et al.; "Dissection of the two transferase activities of the *Pasterurella multocida* hyaluronan synthase: two active sites exist in one polypeptide"; Glycobiology, 10(9):883-889 (2000).
Peppas et al.; "New Challenges in Biomaterials"; Science, 263:1715-1720 (1994).
Manzoni et al.; "Production of K5 Polysaccharides of Different Molecular Weight by *Escherichia coli*"; Journal of Bioactive & Compatible Polymers vol. 11 301-311 (1996).

\* cited by examiner

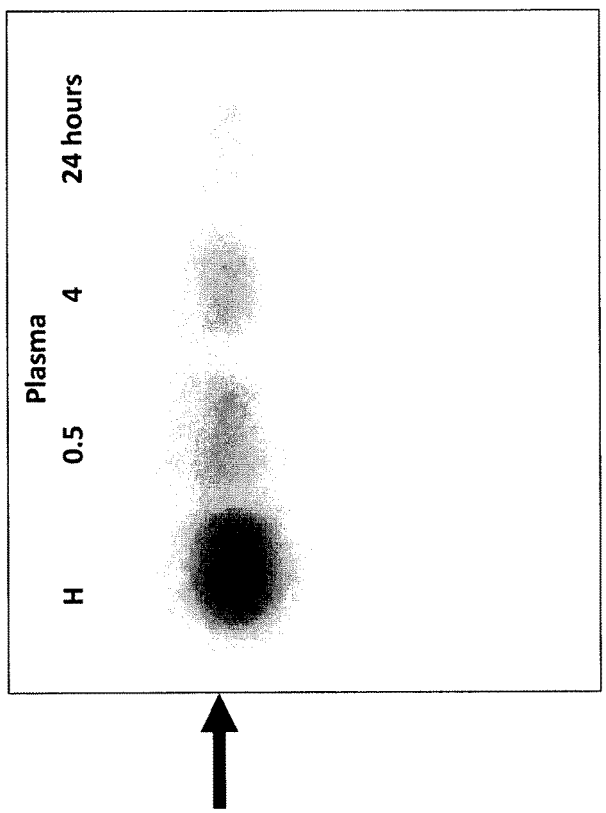
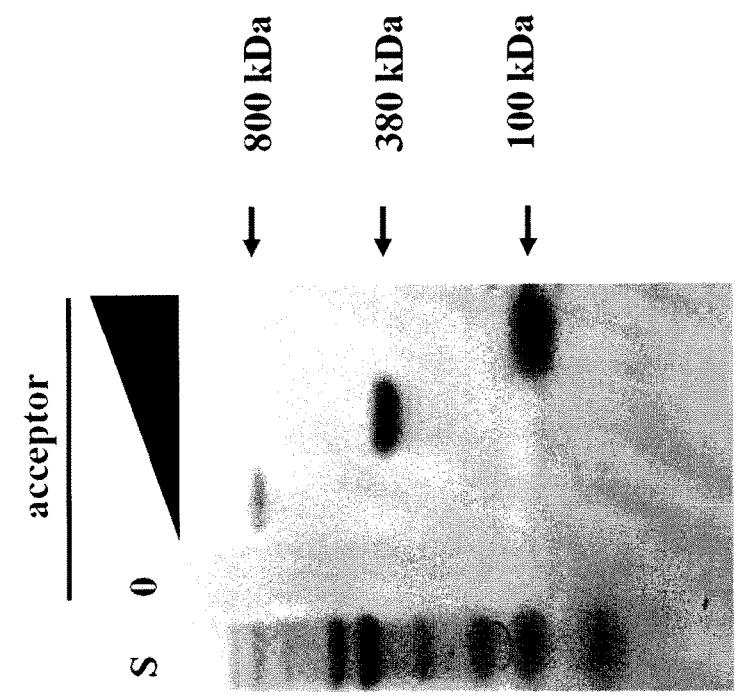

SEQUENCE LISTING

```
<160> NUMBER OF SEQ ID NOS: 2

<210> SEQ ID NO 1
<211> LENGTH: 617
<212> TYPE: PRT
<213> ORGANISM: Pasteurella multocida

<400> SEQUENCE: 1

Met Ser Leu Phe Lys Arg Ala Thr Glu Leu Phe Lys Ser Gly Asn Tyr
1               5                   10                  15

Lys Asp Ala Leu Thr Leu Tyr Glu Asn Ile Ala Lys Ile Tyr Gly Ser
            20                  25                  30

Glu Ser Leu Val Lys Tyr Asn Ile Asp Ile Cys Lys Lys Asn Ile Thr
        35                  40                  45

Gln Ser Lys Ser Asn Lys Ile Glu Glu Asp Asn Ile Ser Gly Glu Asn
    50                  55                  60

Lys Phe Ser Val Ser Ile Lys Asp Leu Tyr Asn Glu Ile Ser Asn Ser
65                  70                  75                  80

Glu Leu Gly Ile Thr Lys Glu Arg Leu Gly Ala Pro Pro Leu Val Ser
                85                  90                  95

Ile Ile Met Thr Ser His Asn Thr Glu Lys Phe Ile Glu Ala Ser Ile
                100                 105                 110

Asn Ser Leu Leu Leu Gln Thr Tyr Asn Asn Leu Glu Val Ile Val Val
            115                 120                 125

Asp Asp Tyr Ser Thr Asp Lys Thr Phe Gln Ile Ala Ser Arg Ile Ala
        130                 135                 140
```

-continued

```
Asn Ser Thr Ser Lys Val Lys Thr Phe Arg Leu Asn Ser Asn Leu Gly
145                 150                 155                 160

Thr Tyr Phe Ala Lys Asn Thr Gly Ile Leu Lys Ser Lys Gly Asp Ile
                165                 170                 175

Ile Phe Phe Gln Asp Ser Asp Val Cys His His Glu Arg Ile Glu
            180                 185                 190

Arg Cys Val Asn Ala Leu Leu Ser Asn Lys Asp Asn Ile Ala Val Arg
        195                 200                 205

Cys Ala Tyr Ser Arg Ile Asn Leu Glu Thr Gln Asn Ile Ile Lys Val
    210                 215                 220

Asn Asp Asn Lys Tyr Lys Leu Gly Leu Ile Thr Leu Gly Val Tyr Arg
225                 230                 235                 240

Lys Val Phe Asn Glu Ile Gly Phe Phe Asn Cys Thr Thr Lys Ala Ser
                245                 250                 255

Asp Asp Glu Phe Tyr His Arg Ile Ile Lys Tyr Tyr Gly Lys Asn Arg
            260                 265                 270

Ile Asn Asn Leu Phe Leu Pro Leu Tyr Tyr Asn Thr Met Arg Glu Asp
        275                 280                 285

Ser Leu Phe Ser Asp Met Val Glu Trp Val Asp Glu Asn Asn Ile Lys
    290                 295                 300

Gln Lys Thr Ser Asp Ala Arg Gln Asn Tyr Leu His Glu Phe Gln Lys
305                 310                 315                 320

Ile His Asn Glu Arg Lys Leu Asn Glu Leu Lys Glu Ile Phe Ser Phe
                325                 330                 335

Pro Arg Ile His Asp Ala Leu Pro Ile Ser Lys Glu Met Ser Lys Leu
            340                 345                 350

Ser Asn Pro Lys Ile Pro Val Tyr Ile Asn Ile Cys Ser Ile Pro Ser
        355                 360                 365

Arg Ile Lys Gln Leu Gln Tyr Thr Ile Gly Val Leu Lys Asn Gln Cys
    370                 375                 380

Asp His Phe His Ile Tyr Leu Asp Gly Tyr Pro Glu Val Pro Asp Phe
385                 390                 395                 400

Ile Lys Lys Leu Gly Asn Lys Ala Thr Val Ile Asn Cys Gln Asn Lys
                405                 410                 415

Asn Glu Ser Ile Arg Asp Asn Gly Lys Phe Ile Leu Leu Glu Lys Leu
            420                 425                 430

Ile Lys Glu Asn Lys Asp Gly Tyr Tyr Ile Thr Cys Asp Asp Ile
        435                 440                 445

Arg Tyr Pro Ala Asp Tyr Ile Asn Thr Met Ile Lys Lys Ile Asn Lys
    450                 455                 460

Tyr Asn Asp Lys Ala Ala Ile Gly Leu His Gly Val Ile Phe Pro Ser
465                 470                 475                 480

Arg Val Asn Lys Tyr Phe Ser Ser Asp Arg Ile Val Tyr Asn Phe Gln
                485                 490                 495

Lys Pro Leu Glu Asn Asp Thr Ala Val Asn Ile Leu Gly Thr Gly Thr
            500                 505                 510

Val Ala Phe Arg Val Ser Ile Phe Asn Lys Phe Ser Leu Ser Asp Phe
        515                 520                 525

Glu His Pro Gly Met Val Asp Ile Tyr Phe Ser Ile Leu Cys Lys Lys
    530                 535                 540

Asn Asn Ile Leu Gln Val Cys Ile Ser Arg Pro Ser Asn Trp Leu Thr
545                 550                 555                 560

Glu Asp Asn Lys Asn Thr Glu Thr Leu Phe His Glu Phe Gln Asn Arg
```

-continued 565 570 575

Asp Glu Ile Gln Ser Lys Leu Ile Ile Ser Asn Asn Pro Trp Gly Tyr
580 585 590

Ser Ser Ile Tyr Pro Leu Leu Asn Asn Asn Ala Asn Tyr Ser Glu Leu
595 600 605

Ile Pro Cys Leu Ser Phe Tyr Asn Glu
610 615

<210> SEQ ID NO 2
<211> LENGTH: 1854
<212> TYPE: DNA
<213> ORGANISM: Pasteurella multocida

<400> SEQUENCE: 2
atgagcttat ttaaacgtgc tactgagcta tttaagtcag gaaactataa agatgcacta 60
actctatatg aaaatatagc taaaatttat ggttcagaaa gccttgttaa atataatatt 120
gatatatgta aaaaaaatat aacacaatca aaaagtaata aaatagaaga agataatatt 180
tctggagaaa acaaattttc agtatcaata aaagatctat ataacgaaat aagcaatagt 240
gaattaggga ttacaaaaga aagactagga gcccccccctc tagtcagtat tataatgact 300
tctcataata cagaaaaatt cattgaagcc tcaattaatt cactattatt gcaaacatac 360
aataacttag aagttatcgt tgtagatgat tatagcacag ataaaacatt tcagatcgca 420
tccagaatag caaactctac aagtaaagta aaaacattcc gattaaactc aaatctaggg 480
acatactttg cgaaaaatac aggaatttta aagtctaaag gagatattat tttctttcag 540
gatagcgatg atgtatgtca ccatgaaaga atcgaaagat gtgttaatgc attattatcg 600
aataaagata atatagctgt tagatgtgca tattctagaa taaatctaga aacacaaaat 660
ataataaaag ttaatgataa taaatacaaa ttaggattaa taactttagg cgtttataga 720
aaagtattta atgaaattgg ttttttttaac tgcacaacca aagcatcgga tgatgaattt 780
tatcatagaa taattaaata ctatggtaaa aataggataa ataacttatt tctaccactg 840
tattataaca caatgcgtga agattcatta ttttctgata tggttgagtg ggtagatgaa 900
aataatataa agcaaaaaac ctctgatgct agacaaaatt atctccatga attccaaaaa 960
atacacaatg aaaggaaatt aaatgaatta aaagagattt ttagctttcc tagaattcat 1020
gacgccttac ctatatcaaa agaaatgagt aagctcagca accctaaaat tcctgtttat 1080
ataaatatat gctcaatacc ttcaagaata aaacaacttc aatacactat tggagtacta 1140
aaaaaccaat gcgatcattt tcatatttat cttgatggat atccagaagt acctgatttt 1200
ataaaaaaac tagggaataa agcgaccgtt attaattgtc aaaacaaaaa tgagtctatt 1260
agagataatg gaaagtttat tctattagaa aaacttataa aggaaaataa agatggatat 1320
tatataactt gtgatgatga tatccggtat cctgctgact acataaacac tatgataaaa 1380
aaaattaata aatacaatga taaagcagca attggattac atggtgttat attcccaagt 1440
agagtcaaca agtatttttc atcagacaga attgtctata attttcaaaa acctttagaa 1500
aatgatactg ctgtaaatat attaggaact ggaactgttg cctttagagt atctattttt 1560
aataaatttt ctctatctga ttttgagcat cctggcatgg tagatatcta tttttctata 1620
ctatgtaaga aaaacaatat actccaagtt tgtatatcac gaccatcgaa ttggctaaca 1680
gaagataaca aaaacactga gaccttattt catgaattcc aaaatagaga tgaaatacaa 1740

```
agtaaactca ttatttcaaa caacccttgg ggatactcaa gtatatatcc attattaaat    1800
aataatgcta attattctga acttattccg tgtttatctt tttataacga gtaa          1854
```

US 9,687,559 B2

HEPAROSAN POLYMERS AND METHODS OF MAKING AND USING SAME FOR THE ENHANCEMENT OF THERAPEUTICS

CROSS-REFERENCE TO RELATED APPLICATIONS

The present application claims benefit under 35 U.S.C. 119(e) of provisional application U.S. Ser. No. 61/179,275, filed May 18, 2009.

The present application is also a continuation-in-part of U.S. Ser. No. 12/383,046, filed Mar. 19, 2009 now abandoned; which claims benefit under 35 U.S.C. 119(e) of provisional applications U.S. Ser. No. 61/095,572, filed Sep. 9, 2008; and U.S. Ser. No. 61/038,027, filed Mar. 19, 2008.

The entire contents of each of the above-referenced patents and patent applications are hereby expressly incorporated herein by reference.

STATEMENT REGARDING FEDERALLY SPONSORED RESEARCH OR DEVELOPMENT

This invention was made with government support under Contract Number MCB9876193 awarded by the National Science Foundation. The government has certain rights in the invention.

BACKGROUND OF THE INVENTION

1. Field of the Invention

The presently claimed and disclosed invention(s) relates, in general, to the field of therapeutics and, more particularly but without limiting, to novel compositions and methods for making heparosan biomaterials that are suitable for conjugation to therapeutics for the purpose of enhancing drug action and/or delivery as well as bioreactive agents for biotechnical applications.

2. Brief Description of the Related Art

Without limiting the scope of the presently claimed and disclosed invention(s), the background of the related art is described in connection with the use of sugar polymers and, more particularly, heparosan as a therapeutic modifying and/or coupling agent.

The presently claimed and disclosed invention(s) relates generally to the field of therapeutics and, more particularly, to the development of enhanced therapeutics through the use of modifying and/or coupling agents and, in particular but without limitation, natural polysaccharides and oligosaccharides such as heparosan. A wide range of existing and near-term therapeutics has great potential, but many possess drawbacks that slow or prevent implementation for aiding human health. Fortunately, the physical, chemical, and/or biological nature of a promising drug candidate may sometimes be assisted by modifying the parental drug. A widely used agent, poly[ethylene glycol] (PEG) has been approved by the Food & Drug Administration (FDA) for use with therapeutic "cargo" including small molecule drugs, polypeptides, and liposomes, for example. The process of adding PEG to a drug, i.e., "PEGylation," has been very successful, as shown in Table 1. The hydrophilic chains of PEG polymers increase the solubility of the cargo in water, protect the cargo when in the human body and prolong the therapeutic action of the cargo. Due to its artificial nature, its chemical synthesis, and its potential harmful effects when ingested in large quantities over long periods of time, the use of PEG has significant drawbacks and alternatives have been sought.

The presently disclosed and claimed invention is directed to such alternative modifying and/or coupling agents, which overcome the defects and disadvantages of the prior art.

DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

FIG. 4 is a pictorial representation showing heparosan is very stable in the mammalian bloodstream. The 100 kDa $^{125}$I-heparosan conjugate was injected intravenously into rats, and at various times, blood was withdrawn, and the plasma was isolated. The samples were deproteinized and analyzed by agarose gel (1.5%) electrophoresis and autoradiography. The molecular weight of starting probe (lane H; arrow) and the polymer in plasma samples are equivalent even after approximately 1-2 days time. Over time, the polymer is removed from circulation within the mammal and then metabolized/excreted.

FIG. 5 is graphical representation showing synthesis of monodisperse heparosan polymers. Three batches of heparosan polymer were analyzed on a 1.2% agarose gel with Stains-all detection. The polymer size is readily controlled (as indicated by the three different size bands of 800 kDa, 380 kDa, and 100 kDa from top to bottom). The tight bands indicate that the products have a narrow size distribution (polydispersity $M_w/M_n=1.06$ to 1.18; for reference, the value of an ideal monodisperse polymer is 1). The size of the polymer affects its half-life in the bloodstream; thus, HEPylation is a means of tuning therapeutic dosing profiles. In addition, the Food & Drug Administration (FDA) regulatory hurdles for production and approval of therapeutics are lower for a more defined, monodisperse molecule in comparison to a less defined, polydisperse molecule.

DETAILED DESCRIPTION OF THE PRESENTLY CLAIMED AND DISCLOSED INVENTION(S)

Figure 1:
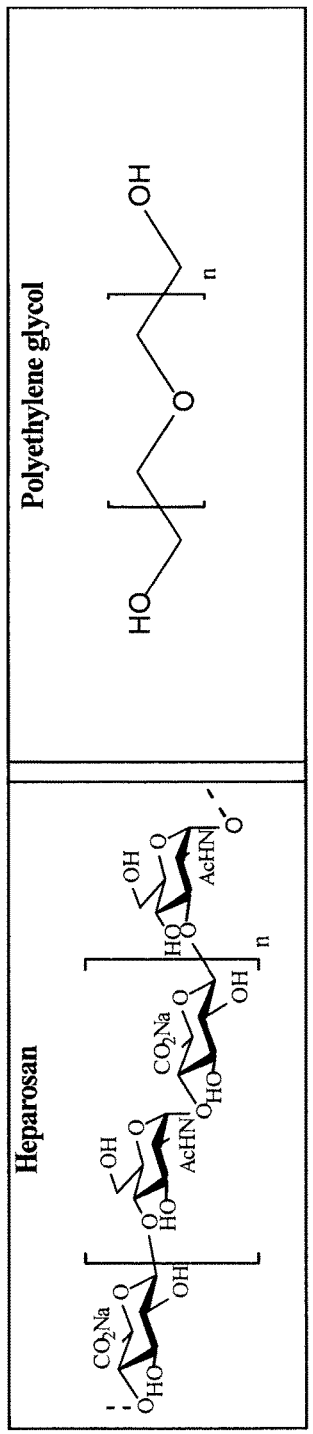
FIG. 1 graphically depicts the structures of heparosan and polyethylene glycol.

Before explaining in detail at least one embodiment of the invention in detail by way of exemplary drawings, figures, graphs, tables, and experimental drafts, for example, it is to be understood that the presently claimed and disclosed invention(s) is not limited in its application to the details of construction and the arrangement of the components set forth in the following description or illustrated in the drawings. The presently claimed and disclosed invention(s) is capable of other embodiments or of being practiced or carried out in various ways. Also, it is to be understood that the phraseology and terminology employed herein is for purpose of description and should not be regarded as limiting. While the making and using of various embodiments of the presently claimed and disclosed invention(s) are discussed in detail below, it should be appreciated that the presently claimed and disclosed invention(s) provide many applicable inventive concepts that can be embodied in a wide variety of specific contexts. The specific embodiments discussed herein are merely illustrative of specific ways to make and use the presently claimed and disclosed invention(s) and do not delimit the scope of the invention.

The needs of the presently claimed and disclosed invention(s) set forth above as well as further and other needs and advantages of the present invention are achieved by the embodiments of the invention described herein below.

The presently claimed and disclosed invention(s) provides for the improvement and enhancement of therapeutics through the conjugation and use of a novel therapeutic modifying agent: heparosan, a natural polysaccharide related to heparin. Heparosan can be synthesized in a step-wise, reproducible, and defined manner so as to provide all of the advantages of PEG without its potential side effects. Heparosan is soluble in water, biocompatible, and bio-inert within the human body.

The addition of heparosan (HEP) to a therapeutic cargo molecule, a process termed herein as "HEPylation", is superior to PEGylation because: a) a larger size range of heparosan polymers is more readily synthesized than PEG; b) the size distribution at longer chain lengths of heparosan can be controlled more carefully than PEG; c) heparosan has a higher water solubility than PEG; d) as a naturally occurring polysaccharide, heparosan's degradation products are biocompatible; and e) heparosan is not immunogenic.

Several linear and branched PEGs having different molecular weights have been employed by those with skill in the art to improve the pharmacokinetic behavior of therapeutic drugs (i.e., the "cargo" carried by the PEG molecule). Several distinct types of reactive PEG polymers allow the synthesis of both reversible and irreversible PEG-drug conjugates. PEG-drug conjugates typically exhibit prolonged residence in vivo, decreased degradation by metabolic enzymes, and reduced immunogenicity. The therapeutic cargo, including proteins and peptides, small molecule drugs, and liposomes, have been PEGylated and evaluated successfully by the FDA (Table 1). Several PEGylated drugs have been in use for more than a decade, thus proving the general applicability and safety of PEGylation. As shown and claimed herein, therapeutic cargo that has been HEPylated (i.e., conjugated to heparosan) retain all of the benefits of PEGylated cargo while minimizing the negative and undesirable attributes of PEG.

Various sized PEGs circulate and are cleared out of the bloodstream of mammals at different periods of times. As shown in Table 2, PEG polymers having a molecular weight of 6,000 Da or 6 kDa (PEG-6) have a shorter half-life in blood serum than PEG polymers having a molecular weight of 170,000 Da or 170 kDa (PEG-170). The half-life of PEG molecules in blood serum is directly dependent upon the size of the polymer. Even though PEGylation may lead to a loss in binding affinity due to steric interference (due to the PEG chain partially covering the drug surface and by conjugating with some of the drugs active sites) with the drug-target binding interaction, the loss in potency is offset by the longer half-life of the PEG drug conjugate circulating in the blood stream. Certain drugs have, therefore, been enabled for use by conjugating the drug to PEG and thereby increasing its half-life within a patient to be treated that otherwise could not have been developed. Much effort is currently ongoing with the goal of improving or re-tooling existing drugs by conjugating with PEG. The novel use of heparosan for a PEG replacement is, therefore, a significant step forward and is providing a highly biocompatible and targeted drug delivery device.

TABLE 1

Currently Marketed PEGylated Drugs
(adapted from 'Pharmacotherapy (2003) 23 (8 pt 2): 3S-8S)

| Cargo of PEG Conjugate | Generic Name (Trade Name)/Manufacturer (FDA Approval Date) | Bioactivity of Native Agent | Main Effect of Pegylation | Reason for Treatment |
|---|---|---|---|---|
| ADA (adenosine deaminase) | Pegademase (ADAGEN/ Enzon (March 1990) | Enzyme replacement, reverses symptoms of ADA deficiency | Longer half-life, reduced immune response | SCID (severe combined immunodeficiency disease) |
| Asparaginase | Pegasparagase (ONCASPAR/ Enzon (February 1994) | Hydrolyzes asparagine, on which leukemic cells are dependent | Longer half-life reduced immune response | In combination chemotherapy for treatment of acute lymphoblastic leukemia in patients hypersensitive to L-asparaginase |
| Granulocyte colony-stimulating factor | Pegfilgrastim (NEULASTA/ Amgen (January 2002) | Stimulation of neutrophil production | Longer half-life, self-regulating clearance | Prophylaxis against severe neutropenia and its complications during myelosuppressive chemotherapy |
| Interferon α2b | Peginterferon α2b (PEGASYS/Roche (October 2002) | Antiviral cytokine | Slower clearance, sustained serum concentration | Hepatitis C in patients with compensated liver disease |
| Stealth PEG liposomes with doxorubicin | Pegylated liposomal doxorubicin (CAELYX DOXIL/Alza (June 1999) | Antitumor anthracycline | Slower clearance, greater distribution into tumors | Refractory ovarian cancer, Kaposi's sarcoma |

TABLE 2

Blood circulation of PEG (adapted from
'J. Phar. Pharm. Sci.' 2000 (3): 125-136)

| Parameter | PEG-6 | PEG-20 | PEG-50 | PEG-170 |
|---|---|---|---|---|
| AUC | 6.2 | 110 | 600 | 1110 |
| $t_{1/2}$, minutes | 17.6 | 170 | 990 | 1390 |

AUC = area under the curve;
$t_{1/2}$ = half life

The main pharmacokinetic outcomes of PEGylation are summarized as changes occurring in the overall circulation life-span within blood serum, tissue distribution pattern, and elimination pathway of the drug PEG conjugate (Table 3). As with PEG, heparosan maintains all of the benefits of PEG while improving bio-compatibility and the ability to selectively produce and target polymers of a desired predetermined size (Sismey-Ragatz et al., J. Biol. Chem, 2007). As with PEG conjugation, conjugation of a drug or therapeutic molecule with heparosan (1) increases retention of the drug in the circulation by protecting against enzymatic digestion, (2) slows filtration by the kidneys, and (3) reduces the generation of neutralizing antibodies. In all respects, HEPylation is a clear substitute for PEGylation and, as a naturally occurring polysaccharide, brings with it an enhanced bio-compatibility and simpler sugar conjugation chemistry.

TABLE 3

Beneficial Features of Therapeutic Modifying Agents: PEGylation versus HEPylation

|  | PEG | Heparosan HEPylation |
|---|---|---|
| a. Extend Cargo Half-life in Bloodstream? (e.g., avoid renal clearance if larger molecular weight) | Yes | Yes |
| b. Protect Cargo from Degradation? (e.g., by proteases) | Yes | Yes |
| c. Shield Cargo from Immune Response? (e.g., prevent antibody generation) | Yes | Yes |
| d. Trap cargo in Cancerous Regions? (e.g., due to altered tumor vasculature) | Yes | Yes |
| e. Enhance Solubility of Cargo? (e.g., especially hydrophobic chemotherapy agents)? | Yes | Yes, increased solubility potential than PEG due to its more hydrophilic nature |
| f. Variety of Cargo Coupling Chemistries? (e.g., amine, sulfhydryl reactive) | Yes | Yes |
| g. Exhance Cargo Stability? (e.g., prevent protein unfolding events) | Yes | Yes |
| h. Reduce Dosage and Maintain Constant Blood Concentrations? (e.g., avoid peaks and troughs; predictable dosing plateau in desired range) | Yes | Yes |
| i. Suitability for a Range of Cargo: (e.g., platform technology) |  |  |
| proteins, peptides? | Yes | Yes |
| small MW drugs? | Yes | Yes |
| liposomes? | Yes | Yes |
| hormones? | Yes | Yes |

First, the nature of degradation of artificial PEG may be a limiting factor for pharmaceuticals used at high doses and/or for long duration treatments. Second, the quality control of PEG polymer synthesis with respect to molecular weight distribution is not as great as desired.

Certain carbohydrates play roles in forming and maintaining the structures of multicellular organisms in addition to more familiar roles as nutrients for energy. Glycosaminoglycans (GAGs) are long linear polysaccharides comprising disaccharide repeats that contain an amino sugar. GAGs are well known to be essential in vertebrates.

The GAG structures possess a significant number of negative groups and hydroxyl groups and are, therefore, highly hydrophilic. Depending on the tissue and cell type, the GAGs are structural, adhesion, and/or signaling elements in humans. A few microbes also produce extracellular polysaccharide coatings called capsules that are composed of GAG chains and that serve as virulence factors. The capsule assists in the microbe's evasion of host defenses such as phagocytosis and complement. As the microbial polysaccharide is identical or very similar to the host GAG, the antibody response to the microbe is either very limited or non-existent.

In humans, polymers of heparosan (also called N-acetyl-heparosan or unsulfated, unepimerized heparin; [4-GlcUA-beta-1,4-GlcNAc-alpha-1-]$_n$; shown in FIG. 1) only exist transiently, serving as a precursor to the more highly modified final products of heparan sulfate and heparin. The bacterial-derived enzymes used to produce heparosan for use in one embodiment of the presently claimed and disclosed invention(s) synthesize heparosan as their final product. A single polypeptide, the heparosan synthase PmHS1 of *Pasteurella multocida* Type D, polymerizes the heparosan sugar chain by transferring both GlcUA and GlcNAc. PmHS1 is a robust enzyme that efficiently makes polymers up to ~1 MDa (1,000 kDa or ~5,000 monosaccharide units) in vitro. In *Escherichia coli* K5, at least two enzymes, KfiA, the alpha-GlcNAc transferase, and KfiC, the beta-GlcUA-transferase, (and perhaps KfiB, a protein of unknown function) work in concert to form the disaccharide repeat of heparosan. The *E. coli* enzyme complex is not as efficient as the PmHS1 enzyme as it is more difficult to produce the long polymer chains with the *E. coli* enzyme complex. However, for the purpose of the presently claimed and disclosed invention(s), it is intended and would be understood by one of skill in the art that any method which produces heparosan may be used. It is not the method of producing heparosan that is determinative—rather, it is the conjugation of heparosan from any source or method of production (e.g., fermented heparosan produced by native or recombinant microbes, as well as chemoenzymatic syntheses or organic chemical syntheses) to a target molecule (i.e., the cargo) for increased solubility in water, bioavailability and dwell time within the patient that is presently disclosed and claimed.

A key advantage to using heparosan is that it has increased biostability in the extracellular matrix when compared to other GAGs such as hyaluronic acid and chondroitin. As with most compounds synthesized in the body, new molecules are typically made, and after serving their purpose, are broken down into smaller constituents for recycling.

Heparin and heparan sulfate, for example, are degraded by a single enzyme known as heparanase. Experimental challenge of heparosan and N-sulfo-heparosan with heparanase, however, shows that since these polymers lack the O-sulfation of heparin and heparan sulfate, heparosan and N-sulfo-heparosan are not sensitive to enzymatic action in vitro by heparanase. These findings indicate that heparosan is not fragmented enzymatically in the body, thereby indicating that heparosan is a stable biomaterial for use as a drug conjugate.

However, if heparosan or any of its fragments (generated by reactive oxygen species, etc.) is internalized into the lysosome, then the molecules will be degraded by resident beta-glucosidase and beta-hexosaminidase enzymes (which remove one sugar at a time from the non-reducing termini of the GAG chain), similar to the degradation of heparin or hyaluronic acid. Therefore, the heparosan polymer is biodegradable and will not permanently reside in the body and thereby cause a lysosomal storage problem. A key advantage for therapeutic modification with heparosan polymer, HEPylation, is that normal monosaccharides, GlcNAc and GlcUA are the products of the eventual degradation. In contrast, PEG degrades into reactive artificial aldehydes and ketones which are toxic above certain levels. PEG also accumulates in the body, especially when present as one or more high molecular weight polymers.

The normal roles of heparin/heparan sulfate in vertebrates include binding coagulation factors (inhibiting blood clotting) and growth factors (signaling cells to proliferate or differentiate). The key structures of heparin/heparan sulfate that are recognized by these factors include a variety of O-sulfation patterns and the presence of iduronic acid [IdoUA]; in general, polymers without these modifications do not stimulate clotting or cell growth. Heparosan-based materials which do not have such O-sulfation patterns, therefore, do not provoke unwanted clotting or cellular growth/modulation. As such, HEPylated drug conjugates do not initiate clotting and/or cell growth processes and remain solely bio-reactive as per the drug or cargo constituent—the heparosan is thus termed or deemed to be biologically inert.

Foreign or unnatural molecules stimulate the immune system. Heparosan polymer exists transiently during heparan sulfate and heparin biosynthesis as well as being found in very short polymer structures within mature heparan sulfate or heparin chains. In the latter case, the N- and O-sulfation reactions are not complete in mammals, so traces of the original heparosan remain; for example, approximately 1-5 unsulfated disaccharide repeats can be interspersed within the sulfated regions. Therefore, the body treats heparosan as 'self,' and does not mount an immune response. $P.$ $multocida$ Type D and $E.$ $coli$ K5 utilize heparosan coatings to ward off host defenses by acting as molecular camouflage. Indeed, scientists had to resort to using capsule-specific phages or selective GAG-degrading enzymes to type these heparosan-coated microbes since a conventional antibody or serum could not be generated—the heparosan is thus termed or deemed non-immunogenic or non-antigenic.

To facilitate the understanding of the presently claimed and disclosed invention(s), a number of terms are defined below. Terms defined herein have meanings as commonly understood by a person of ordinary skill in the areas relevant to the presently claimed and disclosed invention(s). Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims. Generally, all technical terms or phrases appearing herein (unless defined explicitly differently herein) are used as one skilled in the art would understand to be their ordinary meaning. It is contemplated that any embodiment discussed in this specification can be implemented with respect to any method, kit, reagent, or composition of the presently claimed and disclosed invention(s), and vice versa. Furthermore, compositions of the presently claimed and disclosed invention(s) can be used to achieve methods of the presently claimed and disclosed invention(s).

All publications and patent applications mentioned in the specification are indicative of the level of skill of those skilled in the art to which the presently claimed and disclosed invention(s) pertains. All publications and patent applications (including issued patents) are herein incorporated by reference to the same extent as if each individual publication or patent application was specifically and individually indicated to be incorporated by reference in its entirety.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this specification, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context. All of the compositions and/or methods disclosed and claimed herein can be made and executed without undue experimentation in light of the present disclosure.

Heparosan is a sugar polymer of the formula -[GlcNAc-alpha4-GlcUA-beta4]$_n$- where n is from 2 to about 5,000. The term "oligosaccharide" generally denotes n being from about 1 to about 11 while the term "polysaccharide" denotes n being equal to or greater than 12. The term "conjugate" as used herein refers to a complex created between two or more compounds by covalent or weak bonds. The term "cargo" as used herein refers to the drug, therapeutic or other biologically active component in the conjugate, while the term "vehicle" as used herein refers to the carrier of the cargo (e.g., the heparosan polymer) in the conjugate.

As used herein, the term "active agent(s)," "active ingredient(s)," "pharmaceutical ingredient(s)," "therapeutic," "medicant," "medicine," "biologically active compound" and "bioactive agent(s)" are defined as drugs and/or pharmaceutically active ingredients. The presently claimed and disclosed invention(s) may be used to encapsulate, attach, bind or otherwise be used to affect the storage, stability, longevity and/or release of any of the following drugs as the pharmaceutically active agent in a composition. One or more of the following bioactive agents listed in (A)-(X) below may be combined with one or more carriers (however, said listing of agents provided in (A)-(X) is to be understood to be simply for illustration purposes, and is not to be construed as limiting):

(A) Analgesic anti-inflammatory agents such as, acetaminophen, aspirin, salicylic acid, methyl salicylate, choline salicylate, glycol salicylate, 1-menthol, camphor, mefenamic acid, fluphenamic acid, indomethacin, diclofenac, alclofenac, ibuprofen, ketoprofen, naproxene, pranoprofen, fenoprofen, sulindac, fenbufen, clidanac, flurbiprofen, indoprofen, protizidic acid, fentiazac, tolmetin, tiaprofenic acid, bendazac, bufexamac, piroxicam, phenylbutazone, oxyphenbutazone, clofezone, pentazocine, mepirizole, and the like.

(B) Drugs having an action on the central nervous system, for example sedatives, hypnotics, antianxiety agents, analgesics and anesthetics, such as, chloral, buprenorphine, naloxone, haloperidol, fluphenazine, pentobarbital, phenobarbital, secobarbital, amobarbital, cydobarbital, codeine, lidocaine, tetracaine, dyclonine, dibucaine, cocaine, procaine, mepivacaine, bupivacaine, etidocaine, prilocaine, benzocaine, fentanyl, nicotine, and the like. Local anesthetics such as, benzocaine, procaine, dibucaine, lidocaine, and the like.

(C) Antihistaminics or antiallergic agents such as, diphenhydramine, dimenhydrinate, perphenazine, triprolidine, pyrilamine, chlorocyclizine, promethazine, carbinoxamine, tripelennamine, brompheniramine, hydroxyzine, cyclizine, meclizine, clorprenaline, terfenadine, chlorpheniramine, and the like. Anti-allergenics such as, antazoline, methapyrilene, chlorpheniramine, pyrilamine, pheniramine, and the like. Decongestants such as, phenylephrine, ephedrine, naphazoline, tetrahydrozoline, and the like.

(D) Antipyretics such as, aspirin, salicylamide, non-steroidal anti-inflammatory agents, and the like. Antimigrane agents such as, dihydroergotamine, pizotyline, and the like. Acetonide anti-inflammatory agents, such as hydrocortisone, cortisone, dexamethasone, fluocinolone, triamcinolone, medrysone, prednisolone, flurandrenolide, prednisone, halcinonide, methylprednisolone, fludrocortisone, corticosterone, paramethasone, betamethasone, ibuprophen, naproxen, fenoprofen, fenbufen, flurbiprofen, indoprofen, ketoprofen, suprofen, indomethacin, piroxicam, aspirin, salicylic acid, diflunisal, methyl salicylate, phenylbutazone, sulindac, mefenamic acid, meclofenamate sodium, tolmetin, and the like. Muscle relaxants such as, tolperisone, baclofen, dantrolene sodium, cyclobenzaprine.

(E) Steroids such as, androgenic steroids, such as, testosterone, methyltestosterone, fluoxymesterone, estrogens such as, conjugated estrogens, esterified estrogens, estropipate, 17-β estradiol, 17-β estradiol valerate, equilin, mestranol, estrone, estriol, 17β ethinyl estradiol, diethylstilbestrol, progestational agents, such as, progesterone, 19-norprogesterone, norethindrone, norethindrone acetate, melengestrol, chlormadinone, ethisterone, medroxyprogesterone acetate, hydroxyprogesterone caproate, ethynodiol diacetate, norethynodrel, 17-α hydroxyprogesterone, dydrogesterone, dimethisterone, ethinylestrenol, norgestrel, demegestone, promegestone, megestrol acetate, and the like.

(F) Respiratory agents such as, theophilline and β2-adrenergic agonists, such as, albuterol, terbutaline, metaproterenol, ritodrine, carbuterol, fenoterol, quinterenol, rimiterol, solmefamol, soterenol, tetroquinol, and the like. Sympathomimetics such as, dopamine, norepinephrine, phenylpropanolamine, phenylephrine, pseudoephedrine, amphetamine, propylhexedrine, arecoline, and the like.

(G) Antimicrobial agents including antibacterial agents, antifungal agents, antimycotic agents and antiviral agents; tetracyclines such as, oxytetracycline, penicillins, such as, ampicillin, cephalosporins such as, cefalotin, aminoglycosides, such as, kanamycin, macrolides such as, erythromycin, chloramphenicol, iodides, nitrofrantoin, nystatin, amphotericin, fradiomycin, sulfonamides, purrolnitrin, clotrimazole, miconazole chloramphenicol, sulfacetamide, sulfamethazine, sulfadiazine, sulfamerazine, sulfamethizole and sulfisoxazole; antivirals, including idoxuridine; clarithromycin; and other anti-infectives including nitrofurazone, and the like.

(H) Antihypertensive agents such as, clonidine, α-methyldopa, reserpine, syrosingopine, rescinnamine, cinnarizine, hydrazine, prazosin, and the like. Antihypertensive diuretics such as, chlorothiazide, hydrochlorothrazide, bendoflumethazide, trichloromethiazide, furosemide, tripamide, methylclothiazide, penfluzide, hydrothiazide, spironolactone, metolazone, and the like. Cardiotonics such as, digitalis, ubidecarenone, dopamine, and the like. Coronary vasodilators such as, organic nitrates such as, nitroglycerine, isosorbitol dinitrate, erythritol tetranitrate, and pentaerythritol tetranitrate, dipyridamole, dilazep, trapidil, trimetazidine, and the like. Vasoconstrictors such as, dihydroergotamine, dihydroergotoxine, and the like. β-blockers or antiarrhythmic agents such as, timolol pindolol, propranolol, and the like. Humoral agents such as, the prostaglandins, natural and synthetic, for example PGE1, PGE2α, and PGF2α, and the PGE1 analog misoprostol. Antispasmodics such as, atropine, methantheline, papaverine, cinnamedrine, methscopolamine, and the like.

(I) Calcium antagonists and other circulatory organ agents, such as, aptopril, diltiazem, nifedipine, nicardipine, verapamil, bencyclane, ifenprodil tartarate, molsidomine, clonidine, prazosin, and the like. Anti-convulsants such as, nitrazepam, meprobamate, phenyloin, and the like. Agents for dizziness such as, isoprenaline, betahistine, scopolamine, and the like. Tranquilizers such as, reserprine, chlorpromazine, and antianxiety benzodiazepines such as, alprazolam, chlordiazepoxide, clorazeptate, halazepam, oxazepam, prazepam, clonazepam, flurazepam, triazolam, lorazepam, diazepam, and the like.

(J) Antipsychotics such as, phenothiazines including thiopropazate, chlorpromazine, triflupromazine, mesoridazine, piperacetazine, thioridazine, acetophenazine, fluphenazine, perphenazine, trifluoperazine, and other major tranquilizers such as, chlorprathixene, thiothixene, haloperidol, bromperidol, loxapine, and molindone, as well as those agents used at lower doses in the treatment of nausea, vomiting, and the like.

(K) Drugs for Parkinson's disease, spasticity, and acute muscle spasms such as levodopa, carbidopa, amantadine, apomorphine, bromocriptine, selegiline (deprenyl), trihexyphenidyl hydrochloride, benztropine mesylate, procyclidine hydrochloride, baclofen, diazepam, dantrolene, and the like. Respiratory agents such as, codeine, ephedrine, isoproterenol, dextromethorphan, orciprenaline, ipratropium bromide, cromglycic acid, and the like. Non-steroidal hormones or antihormones such as, corticotropin, oxytocin, vasopressin, salivary hormone, thyroid hormone, adrenal hormone, kallikrein, insulin, oxendolone, and the like.

(L) Vitamins such as, vitamins A, B, C, D, E and K and derivatives thereof, calciferols, mecobalamin, and the like for dermatologically use. Enzymes such as, lysozyme, urokinaze, and the like. Herbal medicaments or crude extracts such as, Aloe vera, and the like.

(M) Antitumor agents such as, 5-fluorouracil and derivatives thereof, krestin, picibanil, ancitabine, cytarabine, and the like. Anti-estrogen or anti-hormone agents such as, tamoxifen or human chorionic gonadotropin, and the like. Miotics such as pilocarpine, and the like.

(N) Cholinergic agonists such as, choline, acetylcholine, methacholine, carbachol, bethanechol, pilocarpine, muscarine, arecoline, and the like. Antimuscarinic or muscarinic cholinergic blocking agents such as, atropine, scopolamine, homatropine, methscopolamine, homatropine methylbromide, methantheline, cyclopentolate, tropicamide, propantheline, anisotropine, dicyclomine, eucatropine, and the like.

(O) Mydriatics such as, atropine, cyclopentolate, homatropine, scopolamine, tropicamide, eucatropine, hydroxyamphetamine, and the like. Psychic energizers such as 3-(2-aminopropy)indole, 3-(2-aminobutyl)indole, and the like.

(P) Antidepressant drugs such as, isocarboxazid, phenelzine, tranylcypromine, imipramine, amitriptyline, trimipramine, doxepin, desipramine, nortriptyline, protriptyline, amoxapine, maprotiline, trazodone, and the like.

(Q) Anti-diabetics such as, insulin, and anticancer drugs such as, tamoxifen, methotrexate, and the like.

(R) Anorectic drugs such as, dextroamphetamine, methamphetamine, phenylpropanolamine, fenfluramine, diethylpropion, mazindol, phentermine, and the like.

(S) Anti-malarials such as, the 4-aminoquinolines, alphaaminoquinolines, chloroquine, pyrimethamine, and the like.

(T) Protein therapeutics such as enzymes, cytokines, growth factors, hormones, receptors, antibodies, immune complexes, and the like. Also included are protein derivatives that enhance or block the activity of any of the naturally-occurring or isolated molecules listed herein or interacting components in the biochemical or cellular pathways.

(U) Anti-ulcerative agents such as, misoprostol, omeprazole, enprostil, and the like. Antiulcer agents such as, allantoin, aldioxa, alcloxa, N-methylscopolamine methylsulfate, and the like. Antidiabetics such as insulin, and the like.

(V) Anti-cancer agents such as, cis-platin, actinomycin D, doxorubicin, vincristine, vinblastine, etoposide, amsacrine, mitoxantrone, tenipaside, taxol, colchicine, cyclosporin A, phenothiazines or thioxantheres.

(W) For use with vaccines, one or more antigens, such as, natural, heat-killer, inactivated, synthetic, peptides and even T cell epitopes (e.g., GADE, DAGE, MAGE, etc.) and the like.

(X) Example therapeutic or active agents also include water soluble or poorly soluble drugs of molecular weights from 40 to 1,100 including the following: Hydrocodone, Lexapro, Vicodin, Effexor, Paxil, Wellbutrin, Bextra, Neurontin, Lipitor, Percocet, Oxycodone, Valium, Naproxen, Tramadol, Ambien, Oxycontin, Celebrex, Prednisone, Celexa, Ultracet, Protonix, Soma, Atenolol, Lisinopril, Lortab, Darvocet, Cipro, Levaquin, Ativan, Nexium, Cyclobenzaprine, Ultram, Alprazolam, Trazodone, Norvasc, Biaxin, Codeine, Clonazepam, Toprol, Zithromax, Diovan, Skelaxin, Klonopin, Lorazepam, Depakote, Diazepam, Albuterol, Topamax, Seroquel, Amoxicillin, Ritalin, Methadone, Augmentin, Zetia, Cephalexin, Prevacid, Flexeril, Synthroid, Promethazine, Phentermine, Metformin, Doxycycline, Aspirin, Remeron, Metoprolol, Amitriptyline, Advair, Ibuprofen, Hydrochlorothiazide, Crestor, Acetaminophen, Concerta, Clonidine, Norco, Elavil, Abilify, Risperdal, Mobic, Ranitidine, Lasix, Fluoxetine, Coumadin, Diclofenac, Hydroxyzine, Phenergan, Lamictal, Verapamil, Guaifenesin, Aciphex, Furosemide, Entex, Metronidazole, Carisoprodol, Propoxyphene, Digoxin, Zanaflex, Clindamycin, Trileptal, Buspar, Keflex, Bactrim, Dilantin, Flomax, Benicar, Baclofen, Endocet, Avelox, Lotrel, Inderal, Provigil, Zantac, Fentanyl, Premarin, Penicillin, Claritin, Reglan, Enalapril, Tricor, Methotrexate, Pravachol, Amiodarone, Zelnorm, Erythromycin, Tegretol, Omeprazole, and Meclizine.

The drugs mentioned above may be used in combination as required. Moreover, the above drugs may be used either in the free form or, if capable of forming salts, in the form of a salt with a suitable acid or base. If the drugs have a carboxyl group, their esters may be employed.

The "suitable acid" may be an organic acid, for example, methanesulfonic acid, lactic acid, tartaric acid, fumaric acid, maleic acid, acetic acid, or an inorganic acid, for example, hydrochloric acid, hydrobromic acid, phosphoric acid or sulfuric acid. The base may be an organic base, for example, ammonia, triethylamine, or an inorganic base, for example, sodium hydroxide or potassium hydroxide. The esters may be alkyl esters, aryl esters, aralkyl esters, and the like.

Bioactive Delivery of the Heparosan Conjugate

The heparosan conjugate may be administered parenterally, intraperitoneally, intraspinally, intravenously, intramuscularly, intravaginally, subcutaneously, intranasally, rectally, or intracerebrally. Dispersions of the heparosan conjugate may be prepared in glycerol, liquid poly[ethylene glycols], and mixtures thereof, as well as in oils. Under ordinary conditions of storage and use, such preparations of the heparosan conjugate may also contain a preservative to prevent the growth of microorganisms.

Pharmaceutical compositions suitable for injection use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The heparosan conjugate may be used in conjunction with a solvent or dispersion medium containing, for example, water, ethanol, polyol (for example, glycerol, propylene glycol, and liquid poly[ethylene glycol], and the like), suitable mixtures thereof, vegetable oils, and combinations thereof.

The proper fluidity of the heparosan conjugate may be maintained, for example, by the use of a coating such as lecithin, by the maintenance of the required particle size in the case of dispersion, and/or by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin.

Sterile injectable solutions may be prepared by incorporating the heparosan conjugate in the required amount in an appropriate solvent with one or a combination of ingredients enumerated above, as required, followed by filtered sterilization. Generally, dispersions are prepared by incorporating the heparosan conjugate into a sterile carrier that contains a basic dispersion medium and the required other ingredients from those enumerated above. In the case of sterile powders for the preparation of sterile injectable solutions, the methods of preparation may include vacuum drying, spray drying, spray freezing and freeze-drying that yields a powder of the active ingredient (i.e., the heparosan conjugate) plus any additional desired ingredient from a previously sterile-filtered solution thereof.

The heparosan conjugate may be orally administered, for example, with an inert diluent or an assimilable edible carrier. The heparosan conjugate and other ingredients may also be enclosed in a hard or soft shell gelatin capsule, compressed into tablets, or incorporated directly into the subject's diet. For oral therapeutic administration, the heparosan conjugate may be incorporated with excipients and used in the form of ingestible tablets, buccal tablets, troches, capsules, elixirs, suspensions, syrups, wafers, and the like. The percentage of the heparosan conjugate in the compositions and preparations may, of course, be varied as will be known to the skilled artisan. The amount of the heparosan conjugate in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of heparosan conjugate calculated to produce the desired therapeutic effect. The specification for the dosage unit forms of the presently claimed and disclosed invention(s) are dictated by and directly dependent on (a) the unique characteristics of the heparosan conjugate and the particular therapeutic effect to be achieved, and (b) the limitations inherent in the art of compounding such a therapeutic compound for the treatment of a selected condition in a subject.

Aqueous compositions of the present invention comprise an effective amount of the nanoparticle, nanofibril or nanoshell or chemical composition of the presently claimed and disclosed invention(s) dissolved and/or dispersed in a pharmaceutically acceptable carrier and/or aqueous medium. The biological material should be extensively dialyzed to remove undesired small molecular weight molecules and/or lyophilized for more ready formulation into a desired vehicle, where appropriate. The active compounds may generally be formulated for parenteral administration, e.g., formulated for injection via the intravenous, intramuscular, sub-cutaneous, intralesional, and/or even intraperitoneal routes. The preparation of an aqueous composition that contains an effective amount of the nanoshell composition as an active component and/or ingredient will be known to those of skill in the art in light of the present disclosure. Typically, such compositions may be prepared as injectables, either as liquid solutions and/or suspensions; solid forms suitable for using to prepare solutions and/or suspensions upon the addition of a liquid prior to injection may also be prepared; and/or the preparations may also be emulsified. Also, the heparosan vehicle can be used to enhance a secondary vehicle (e.g., liposomes, nanoparticles, etc.) that acts as a carrier or adjuvant for a drug.

Examples are provided hereinbelow. However, the present invention is to be understood to not be limited in its application to the specific experimentation, results and laboratory procedures. Rather, the Examples are simply provided as one of various embodiments and is meant to be exemplary, not exhaustive.

Example 1

Defined GAG synthesis and heparosan synthesis in particular is rather versatile with respect to chemical functionality as well as size control. For example, U.S. Publication No. US 2008/0109236 A1 (U.S. patent application Ser. No. 11/906,704 filed Oct. 3, 2007, entitled "PRODUCTION OF DEFINED MONODISPERSE HEPAROSAN POLYMERS AND UNNATURAL POLYMERS WITH POLYSACCHARIDE SYNTHASES") discloses a methodology for polymer grafting utilizing heparin/heparosan synthases from *Pasteurella* in order to provide heparosan polymers having a targeted size and that are substantially monodisperse at the desired size ranges. As disclosed in the '704 application, appropriate reactive moieties may be added to the heparosan polymer at the reducing or non-reducing termini or throughout the sugar chain. Having one reactive group/chain is preferable when conjugating the heparosan polymer to its cargo. As such, the methodology of the '704 application can be applied to produce heparosan polymers suitable for HEPylation with a cargo molecule. Table 4 lists different HEPylation polymer chemistries which are available and/or suitable for modifying the heparosan polymer to make it more acceptable or suitable for conjugating with specific cargo molecules. It is not the nature or manner of the complexation or conjugation between heparosan and the drug (by any covalent chemical or weak bond) that is controlling; rather, it is the particular use to which the heparosan will be put.

TABLE 4

Heparosan Polymer Chemistries Available

| Functional Group | Number of Extra Steps* | Reactive with: | Position on Heparosan | Typical Cargo | Notes |
|---|---|---|---|---|---|
| 1. aldehyde | 0 | amines | Reducing | Peptide, Protein | Irreversible if NaCNBH$_3$ coupling |
| 2. malemide | 2 | sulfhydryls | Reducing | Peptide, Protein | Irreversible |
| 3. pyridylthio | 2 | sulfhydryls | Reducing | Peptide, Protein | Reversible (disulfide) |
| 4. Azido | 1 | acetylenes (tripleCC bond) | Non-Reducing Interior | Various | Cu(I) Coupling Irreversible |
| 5. Amino | 1 | aldehydes | Reducing Non-reducing Interior | Drugs | NaCNBH$_4$ Coupling Irreversible |
| 6. N-hydroxy succimimide (NHS) | 2 | amines | Reducing Non-reducing | Peptide, Protein | Irreversible |
| 7. hydrazide | 1 | aldehydes, ketones | Reducing | Drugs | Irreversible if NaCNBH$_3$ Reversible otherwise |

*beyond "normal heparosan" polymer

PmHS1 (SEQ ID NOS: 1 and 2, the amino acid and nucleotide sequences, respectively) was expressed as a carboxyl terminal fusion to maltose binding protein (MBP) using the pMAL-c2X vector (New England BioLabs). To facilitate extracting the enzymes, the expression host *E. coli* XJa (Zymo Research), which encodes a phage lysin enzyme, was employed and allowed for simple freeze/thaw lysis. Cultures were grown in Superior Broth (AthenaES) at 30° C. with ampicillin (100 µg/ml), and L-arabinose (3.25 mM). At mid-log phase, isopropyl β-D-1-thiogalactopyranoside (IPTG) (0.2 mM final) was added to induce fusion protein production. One hour after induction, the cultures were supplemented with fructose (12.8 mM final) and grown for approximately 5-12 hours before harvesting by centrifugation at 4° C. The bacteria were resuspended in 20 mM Tris, pH 7.2, and protease inhibitor cocktail on ice, then frozen and thawed twice, thus allowing lysin to degrade the cell walls. The lysates were clarified by centrifugation.

The synthase was affinity purified via the MBP unit using amylose resin (New England BioLabs). After washing extensively with column buffer (20 mM Tris, pH 7.2, 200 mM NaCl, 1 mM EDTA), the protein was eluted in column buffer containing 10 mM maltose. Protein concentration was quantitated by the Bradford assay (Pierce, Rockford, Ill.) using a bovine albumin serum standard. The purification was monitored by SDS-PAGE with copper negative staining (which adds comparable sensitivity as conventional silver staining) followed by Coomassie blue staining. The enzyme (approximately 90-95% pure; yield ~10 mg per liter of culture) may be used directly after buffer exchange into 50 mM Tris, pH 7.2, by ultrafiltration. Further purification by anion-exchange chromatography provides an approximately 95-99% pure PmHS1 enzyme.

A heparosan polysaccharide (having a molecular weight of approximately 200-300 kDa) derived from the spent fermentation broth of *P. multocida* Type D cultures was converted into heparosan tetrasaccharide (4-mer, having a molecular weight of approximately 700 Da), the starting material for the primers described later herein. *P. multocida* Type D cells were grown in a proprietary synthetic media at 37° C. in shake flasks for approximately 24 hrs. Spent culture medium (the liquid part of culture after microbial cells were removed) was harvested (by centrifugation at 10,000×g, 20 min) and deproteinized (solvent extraction with chloroform). The very large anionic heparosan polymer ("fermentation heparosan," having a molecular weight of approximately 200-300 kDa) was isolated via ultrafiltration (30 kDa molecular weight cut-off; Amicon) and ion exchange chromatography (NaCl gradient on Q-Sepharose; Pharmacia). Heparosan from *E. coli* K5 cultures can also be used, but the polymers are initially lower molecular weight than *P. multocida* Type D.

Heparosan oligosaccharides ((GlcUA-GlcNAc)$_n$-(GlcUA-anhydromannitol), n=1, 2 or 3) were prepared by partial deacetylation of heparosan polysaccharide with base, nitrous acid hydrolysis, and reduction; these polymers contain intact non-reducing termini, but an anhydromannitol group at the reducing end. The fragments were purified by gel filtration on a P2 column (BioRad, Hercules, Calif.) in 0.2 M ammonium formate, followed by normal phase thin layer chromatography (TLC) on silica plates (Whatman) with n-butanol/acetic acid/water (1:1:1). The bands were detected by staining of side lanes with napthoresorcinol. The size and purity of oligosaccharides were verified by matrix assisted laser desorption ionization time of flight mass spectrometry (MALDI-ToF MS). Alternatively, acid hydrolysis or enzymatic cleavage yields oligosaccharides that can also be employed for use.

Amino-Hep$_4$ was prepared by reductive amination of Hep$_4$, the heparosan tetrasaccharide (n=2), with ammonium ion. The dry sugar was dissolved in anhydrous methanol (0.71 mg/ml w/v or 0.93 mM final) under sonication. After addition of solid ammonium acetate and NaBH$_3$CN (final 1 M and 0.1 M, respectively), the mixture was heated to reflux (approximately 70-80° C.) overnight. Thin layer chromatographic analysis (TLC—silica; BuOH/AcOH/H$_2$O 1:1:1 v:v:v with detection by napthoresorcinol reagent) was used to monitor consumption of the starting material. The reaction was quenched by slow addition of 20% AcOH. The solvent was evaporated in vacuo and the residue dissolved in 0.2 M ammonium formate for desalting by gel filtration chromatography on a P-2 resin column (Bio-Rad) in the same volatile buffer. The fractions containing the target molecule were pooled and lyophilized. The volatile salts were removed by two more cycles of dissolving in water and lyophilization. Flash silica gel column chromatography (silica gel 60, E. Merck; BuOH/AcOH/H$_2$O 1:1:1 v:v:v) was employed for further purification. The structure of the amino-Hep$_4$ product was confirmed by matrix-assisted laser desorption time-of-flight mass spectrometry analysis. The derived amino-HEP4 primer was extended by the PmHS1 enzyme as described in the '704 application to form amino-heparosan polymer used as the carrier portion of the heparosan conjugate.

The Amino-heparosan polymer may be further reacted with various activated bifunctional N-hydroxysuccinimide esters to thereby add desirable groups including maleimides, a sulfhydryl selective reagent, etc. The amino-heparosan polymer was reacted with approximately 10-fold molar excess of (Pierce) in 10% dimethylsulfoxide, 0.1 M potassium phosphate, 0.15 M NaCl, pH 7.4, for 2 hrs at room temperature. The target compound in the reaction mixture was purified by gel filtration chromatography on Sephadex G-25 resin (PD-10, Pharmacia) as detailed above.

The amino-HEP4 products may also be reductively aminated by treatment with adipic acid dihydrazide (30 eq) and sodium cyanoborohydride (100 eq) at 50-60° C. in 1 M sodium phosphate buffer, pH 5.5. After desalting, the obtained hydrazide amino-HEP4 may be further purified by strong anion exchange chromatography using Sepharose Q (Pharmacia) with an ammonium bicarbonate gradient elution. The hydrazide amino-HEP4 primer may also be extended by the PmHS1 enzyme in order to produce polymers having varying sizes as described below.

Synchronized polymerization reactions were used to produce monodisperse polymers as previously described and disclosed in the '704 patent application. The formation of heparosan with narrow size distribution (i.e., monodisperse) is dependent on the ability of the enzyme to be primed by acceptors (thus avoiding a slow de novo initiation event yielding out of step elongation events) and efficiently transfer monosaccharides from UDP-sugars. Recombinant PmHS1 synthesizes heparosan chains in vitro if supplied with both required UDP-sugars according to the equation:

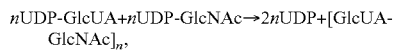
$n$UDP-GlcUA+$n$UDP-GlcNAc→2$n$UDP+[GlcUA-GlcNAc]$_n$,

However, if a heparosan-like oligosaccharide ([GlcUA-GlcNAc])$_x$) is also supplied in vitro, then the overall incorporation rate is elevated up to approximately 25-fold. The rate of initiation of a new chain de novo is slower than the subsequent elongation (i.e., repetitive addition of sugars to a nascent HA molecule). The observed stimulation of synthesis by exogenous acceptor primer appears to operate by bypassing the kinetically slower initiation step, allowing the elongation reaction to predominate as in the following equation:

$n$UDP-GlcUA+$n$UDP-GlcNAc+[GlcUA-GlcNAc]$_x$→2$n$UDP+[GlcUA-GlcNAc]$_{x+n}$ If there are many termini (i.e., z is large), then a limited amount of UDP-sugars will be distributed among many molecules and thus result in many short polymer chain extensions. Conversely, if there are few termini (i.e., z is small), then the limited amount of UDP-sugars will be distributed among few molecules and thus result in long polymer chain extensions. Thus, by controlling the molar ratio of acceptor to UDP-sugar, it is possible to select the final polymer size desired. Typically, from about 50% to about 90% of the starting UDP-sugars are consumed in the reactions on the basis of polysaccharide recovery. Alternatively, if size control is not as critical, then "fermentation heparosan" or its fragments (generated by acid, base, enzyme or physical cleavage methods known to those of skill in the art) will suffice as the vehicle. Similarly, chemically manufactured heparosan may be utilized. As will be appreciated by one of ordinary skill in the art, therefore, it is not the source or manner in which the heparosan is made that is controlling; rather, it is the particular use to which the heparosan will be put. If size is critical, recombinant chemoenzymatic production is preferred. In situations where size is of a secondary or lesser importance, fermentation heparosan (or its derivatives) may be used. As such, the use of heparosan from any source or produced by any methodology is intended to be within the presently claimed and disclosed invention. Likewise, it is not the nature or manner of the complexation between heparosan and the drug (by any chemical or weak bond) that is controlling; rather it is the particular use to which the heparosan will be put.

The yield and molecular weight size distribution of the heparosan is checked by (a) carbazole assays for uronic acid; and (b) agarose gel electrophoresis (1×TAE buffer, 0.8-1.5% agarose) followed by Stains-All detection. The carbazole assay is a spectrophotometric chemical assay that measures the amount of uronic acid in the sample via production of a pink color; every other sugar in the heparosan chain is a glucuronic acid (GlcUA). The heparosan polymer size is determined by comparison to monodisperse HA size standards (HA Lo-Ladder, Hyalose, LLC) run on gels. The detection limit of the carbazole and the gel assays is approximately 5-15 micrograms of polymer. Any endotoxin is removed by passage through an immobilized polymyxin column (Pierce); the material is then tested with a *Limulus* amoebacyte-based assay (www.Cambrex.com) to assure that the heparosan contains <0.05 endotoxin units/mg solid (based on USP guidelines).

Examples of the productions of monodisperse heparosan are shown in FIG. 5 where providing various levels of primer yielded different Mw (weight average molecular mass) products with low polydispersity (Mw/Mn; Mn=number average molecular weight). For reference, the polydispersity value for an ideal monodisperse polymer equals 1. The parallel reaction without an acceptor (lane 0) resulted in a large product that was significantly polydisperse, i.e., it contains heparosan polymers of varying size and length.

The polymerization by synthases in the presence of an acceptor is a synchronized process. Reactions without acceptor exhibit a lag period interspersed with numerous, out of step initiation events that yield a short heparosan oligosaccharide. Once any chain is formed, the heparosan polymer is elongated rapidly. Other new chains that arise later during the lag period are also elongated rapidly, but the size of these younger chains never catches up to the older chains in a reaction with a finite amount of UDP-sugars. In contrast, in reactions containing an acceptor, all heparosan chains are elongated in parallel in a nonprocessive fashion resulting in a more homogenous final polymer population.

The enzymological properties of recombinant pmHS1 described above also allow for the control of heparosan polymer size in chemoenzymatic syntheses. First, as noted above, the rate-limiting step in vitro appears to be the chain initiation step. Therefore, PmHS1 transfers monosaccharides onto the existing heparosan acceptor chains before substantial de novo synthesis. Second, the enzyme polymerizes heparosan in a rapid nonprocessive fashion in vitro. Therefore, the amount of primer should affect the final size of the product when a finite amount of UDP-sugar is present.

The synthase adds all available UDP-sugar precursors to the nonreducing termini of acceptors as in the equation:

$$n\text{UDP-GlcUA} + n\text{UDP-GlcNAc} + z[\text{GlcUA-GlcNAc}]_x \rightarrow 2n\text{UDP} + z[\text{GlcUA-GlcNAc}]_{x+(n/z)}$$

Thus, by controlling the molar ratio of acceptor to UDP-sugar, it is now possible to select the final heparosan polymer size desired. Typically, from about 50% to about 90% of the starting UDP-sugars are consumed in the reactions on the basis of polysaccharide recovery.

The size distribution of the heparosan polymers produced was determined by high performance size exclusion chromatography-multi angle laser light scattering (SEC-MALLS). Polymers (2.5 to 12 μg mass; 50 μl injection) were separated on PL aquagel-OH 30 (8 μm), —OH 40, —OH 50, —OH 60 (15 μm) columns (7.5×300 mm, Polymer Laboratories) in tandem or alone as required by the size range of the polymers to be analyzed. The columns were eluted with 50 mM sodium phosphate, 150 mM NaCl, pH 7 at 0.5 ml/min. MALLS analysis of the eluant was performed by a DAWN DSP Laser Photometer in series with an OPTILAB DSP Interferometric Refractometer (632.8 nm; Wyatt Technology). The ASTRA software package was used to determine the absolute average molecular mass using a dn/dc coefficient of 0.153 determined for HA, a polymer with the exact same sugar composition as heparosan, by Wyatt Technology. The Mw and polydispersity values from at least two SEC-MALLS runs were averaged in order to obtain a final approximation of the Mw and polydispersity of the heparosan molecule.

Although there have been described many different types of molecules that can be conjugated with the heparosan polymer, two primary defined model cargoes are of particular interest and importance: (a) a chemotherapy agent, and (b) a protein therapeutic. For (a), doxorubicin and taxol are useful chemotherapy agents for treating several cancers. Taxol is only slightly soluble in water (i.e., approximately 0.4 micrograms per mL), and such solubility issues can be improved through conjugation with the hydrophilic heparosan polymer. The carbonyl groups found on the taxol or doxorubicin molecule allows the drug to couple monovalently to the heparosan polymer, thereby providing a heparosan drug conjugate. However, if desirable and to increase dosage of pharmaceutical available for pharmacological treatment, the drug molecule is also attachable to multiple positions on the heparosan polymer. A dihydrazide may also be added to the drug-heparosan conjugate in order to create a time-release formulation. The heparosan-doxorubicin or taxol-heparosan conjugate is water-soluble and nontoxic; as heparosan is slowly degraded in blood pH, the linkage releases free active doxorubicin or taxol in a specific and controlled manner.

For (b), protein targets include enzymes, cytokines, interferon, antibodies, receptors and growth factors as well as modified derivatives (e.g., with either chemical or molecular genetic changes). Bovine serum albumin, BSA, is a useful surrogate for testing and modeling a protein therapeutic conjugated with heparosan. The BSA protein does not have intrinsic glycosylation and facilitates analysis of the addition of one or more heparosan chains to the BSA-heparosan conjugate. The use of heparosan as vehicle for drug conjugation is also applicable to recombinant proteins with a bioengineered extra cysteine or an exposed sulfhydryl group, such as antibodies, resulting in an improved strategy to couple such cargo. The cysteine's sulfhydryl group is coupled to the monovalent heparosan-maleimide to provide the heparosan conjugate. Alternatively, heparosan-thio-pyridyl may be used if protein release is desirable due to a reversible disulfide linkage between the sugar polymer (i.e., the heparosan polymer) and the cargo (i.e., recombinant proteins, etc.). As with PEG, the aldehyde of heparosan chains may be coupled to amines of proteins via reductive amination with sodium cyanoborohydride; a useful process for the conjugation of growth factors and interferon.

After the heparosan protein conjugation occurs, the molecule is challenged with (a) proteases and (b) antibodies (e.g., anti-BSA antibody). For protease sensitivity, samples of protein or protein-heparosan are treated with dilution series of trypsin, an aggressive serine protease, for 0-60 min, then run on the SDS-PAGE gel. Relative resistance to digestion occurs for protein-heparosan. For antigenicity, protein or protein-heparosan are incubated with anti-protein IgG beads (e.g., anti-BSA IgG beads from Sigma) for 1 hour in saline, then the supernatant analyzed by PAGE. Alternatively, soluble anti-protein reagent can be incubated with test samples and run on native gels (similar to standard gels except that sample buffer lacks reducing agent and will not be boiled). A higher molecular weight complex forms when the antibody builds to the protein-heparosan conjugate causing a "super-shift". The protein-heparosan conjugate is resistant to anti-protein if the heparosan blocks its epitope. The overall goal is to assess, and to optimize, as needed the reaction parameters to produce the heparosan-conjugate.

A Strategy for HEPylation Reagent Preparation and Utilization

Figure 6:
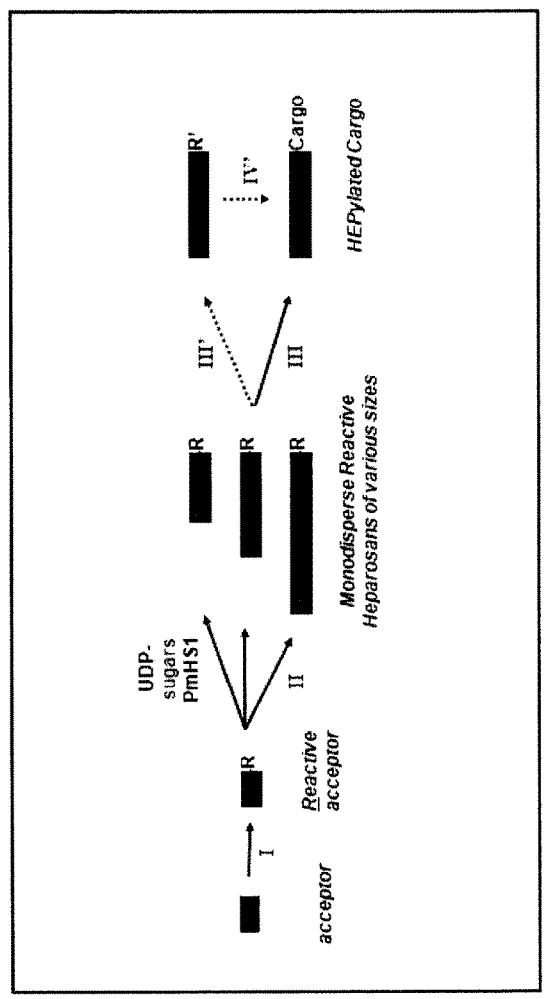
FIG. 6 is a graphical representation of one strategy for HEPylation reagent preparation and utilization to form a therapeutic conjugate. Three or four sequential reactions are used to produce a HEPylated cargo in this embodiment, where activated heparosan vehicle is coupled to a cargo. I. An acceptor (a heparosan tetrasaccharide, Hep$_4$) is modified to add a reactive group (e.g., R=amino or hydrazide). II. Three independent reaction mixtures, each with a different ratio of UDP-sugar/reactive acceptor, are elongated with PmHS1 synthase via polymer grafting to yield a set of distinct reactive monodisperse heparosan polymers of three different sizes. III. The Cargo is modified directly with any one size polymer. III'. Alternatively (dotted line), an additional modification step is used to alter the reactivity of the heparosan reagent (e.g., add a R'=maleimide group onto amino-heparosan) allowing the next step, IV, modification of Cargo. Alternative embodiments include (a) activating heparosan produced by fermentation of bacteria and then coupling to cargo or (b) coupling the activated short acceptor to a cargo, then elongating via polymer grafting to a useful, desired size heparosan chain with heparosan synthase PmHS1.

Three or four sequential reactions were used to produce a HEPylated cargo in this embodiment of drug-conjugate synthesis as in FIG. 6. (1) An acceptor (a heparosan tetrasaccharide, Hep4) was modified to add a reactive group (R=amino or hydrazide). (2) Three independent reaction mixtures, each with a different ratio of UDP-sugar/reactive acceptor, were elongated with PmHS1 synthase to yield a set of distinct reactive monodisperse heparosan polymer preparations of three different sizes. (3) The Cargo was modified directly with any one size polymer. (3A) Alternatively (dotted line), an additional modification step was used to alter the reactivity of the heparosan reagent (add a R'=maleimide group onto amino-heparosan) allowing the next step, (4), modification of the cargo.

There are numerous possibilities for coupling the heparosan vehicle and therapeutic cargo involving various chemistries which include, but are not limited to, the examples listed previously in Table 4. In the examples that follow, two proteins, BSA and IgG antibody, and two small molecules, fluorescein and Bolton-Hunter reagent, were used as cargo for coupling various monodisperse or polydisperse heparosan polymers produced either via fermentation in vivo or chemoenzymatic synthesis in vivo.

Figure 7:
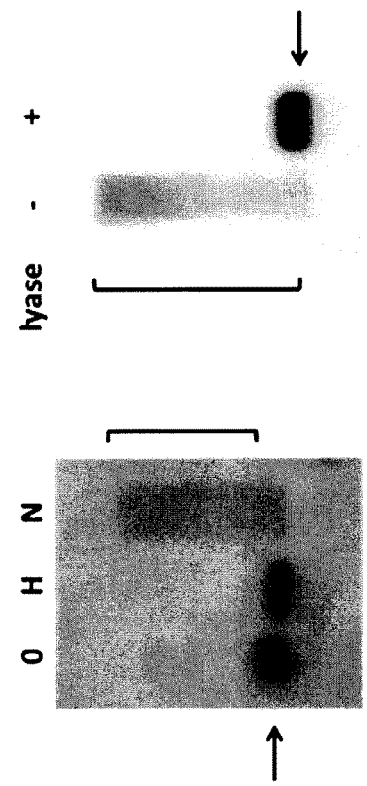
FIG. 7 are pictorial representations of SDS-PAGE gels illustrating the production of HEPylated BSA molecules (left panel) and degradation thereof with heparosan lyase (right panel).
Figure 8:
FIG. 8 are pictorial representations of an SDS-PAGE gel (left panel) and gel filtration chromatography profile (right panel) illustrating production of a series of higher molecular weight products corresponding to a series of HEPylated BSA molecules.

FIGS. 7-8 illustrate the production of HEPylated BSA molecules via chemoenzymatic synthesis. In FIG. 7, radioactive bovine serum albumin [BSA] ([125]I-Bolton-Hunter labeled; migration marked with arrow) protein was reacted via reductive amination with sodium cyanoborohydride with two different reactive 20 kDa heparosan polysaccharides, 'H' or 'N' (unmodified BSA starting material is lane '0'). Each reactive heparosan was made by extending a short oligosaccharide acceptor into a longer 20 kDa polymer with PmHS1 enzyme and UDP-sugars. The acceptors were derived from heparosan polysaccharide (~200-300 kDa) by two different methods: for H, a heparosan tetrasaccharide formed by HCl cleavage with general structure [GlcUA-GlcNAc]$_2$ was used while for N, a heparosan tetrasaccharide formed by base treatment followed by nitrous acid cleavage with general structure [GlcUA-GlcNAc]-GlcUA-anhydromannitol was used. As seen by the SDS-PAGE gel visualized by autoradiography on the left, higher molecular weight products are observed in the N lane, corresponding to a series of HEPylated BSA molecules (see bracketed area). The H lane does not have the same pattern due to the fact that the H polymer must mutarotate to yield a free aldehyde that can react with the BSA amine groups, and thus has lower yields. On the other hand, the N polymer always has a free aldehyde, thus allowing better reaction. As a proof of the HEPylated BSA structure, a duplicate sample of the N material was treated with heparosan lyase, an enzyme that degrades the heparosan polymer but does not degrade other macromolecules such as BSA. As seen in the '+lyase lane,' the BSA now runs at its original position, demonstrating that authentic heparosan chains were added to the protein cargo.

In FIG. 8, bovine serum albumin [BSA] protein was reacted with Traut's reagent (T; iminothiolane) to convert some of its amino groups (lysines and amino termini) into free sulfhydryl groups forming T-BSA; in this case, ~1-3 residues on average were predicted to be modified based on the reaction stoichiometry employed and the general completeness of the reaction. This T-BSA material was incubated with a reactive 75 kDa maleimide heparosan. The reactive heparosan was made by (i) converting a heparosan tetrasaccharide ([GlcUA-GlcNAc]-GlcUA-anhydromannitol) into an amino derivative using reductive amination with sodium cyanoborohydride in the presence of ammonia, (ii) extending this sugar into a longer polymer with PmHS1 enzyme and UDP-sugars, and (ii) reacting the long amino-polymer with a N-hydroxysuccinimide ester of a maleimide-containing compound. As seen by the SDS-PAGE gel visualized by Coomassie staining, a series of higher molecular weight products are observed in the 'Hep' lane corresponding to a series of HEPylated BSA molecules (untreated T-BSA control is in lane 0). The gel filtration chromatography profile (with absorbance at 280 nm detection) confirms that higher molecular weight polymers, HEPylated cargo, were formed. The production of several species is due to the nature of the chemically modified T-BSA (~1 to 3 T reagents/BSA molecule are formed in a rather uncontrolled chemical reaction); if a natural protein or a genetically engineered molecule (e.g., with an extra free cysteine residue) contained only a single sulfhydryl group, then a single mono-HEPylated species would result. In addition, in other embodiments, any sulfhydryl moiety could be used on the cargo (protein or other small molecule or secondary vehicles) as well as any alternative sulfhydryl-reactive reagent on the heparosan polymer including pyridylthiols or haloacids.

Immunoreactivity of many drugs is a serious issue, thus necessitating conjugation or humanization of the drug or the use of very low dosages and/or short treatments. If heparosan is attached to a therapeutic cargo, then it is expected that the cargo surface will be less accessible to antibody binding. The HEPylated BSA material (BSA with one to three 75 kDa heparosan chains/polypeptide) produced in experiments depicted in FIG. 8 was subjected to tests with an anti-BSA polyclonal antibody. To test this hypothesis, the FIG. 8 material (either di-, tri-, or mono-HEPylated BSA—all purified by gel filtration) were compared to BSA and T-BSA (controls) in a radiometric immune assay (RIA) in a competition format (Table 5). First, a capture antibody coating was placed on the surface of a well of a 96-well plate. After blocking with ovalbumin, a solution of one of the 4 test molecules above was added to the wells together with radioactive BSA ([$^{125}$I] Bolton-Hunter labeled). After extensive washing, the wells were counted to measure radioactivity. Each competitor protein was measured at two concentrations, 25 or 500 nanograms (ng). The control wells did not have any BSA competitor, thus representing a 'maximal binding' signal. BSA alone competed for binding with the radioactive probe to immobilized antibody; the signal was substantially reduced by 25 ng of BSA competitor and greatly reduced with 500 nanograms of BSA. T-BSA without heparosan competed in a fashion similar to normal BSA. However, more HEPylated BSA was needed to partially inhibit the radioactive signal, indicating that the antibody did not recognize or bind to the HEPylated molecules as well as BSA or T-BSA. Therefore, HEPylation will help shield cargo from the full brunt of immunological defenses in the mammalian body.

TABLE 5

Radiometric Immune Assay (RIA) comparing HEPylated BSA to BSA and T-BSA

| Sample | [$^{125}$I] cpm Bound |
|---|---|
| No competitor | 1190 |
|  | 1270 |
| BSA, 25 ng | 750 |
|  | 760 |
| BSA, 500 ng | 140 |
|  | 100 |
| T-BSA, 25 ng | 770 |
|  | 830 |
| T-BSA, 500 ng | 140 |
|  | 190 |
| Di,tri-HEP BSA, 25 ng | 1050 |
| Di,tri-HEP BSA, 500 ng | 620 |
| mono-HEP BSA, 25 ng | 1220 |
| mono-HEP BSA, 500 ng | 630 |

Figure 9:
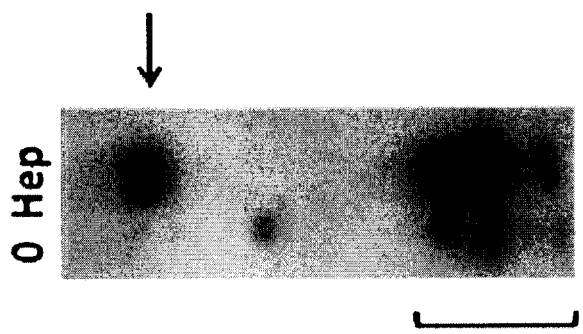
FIG. 9 is a pictorial representation of an SDS-PAGE gel illustrating the production of HEPylated IgG molecules (see arrow area).

FIG. 9 illustrates the production of HEPylated IgG molecules. A preparation of radioactive immunoglobulins [IgG] ($^{125}$I-Bolton-Hunter labeled; migration marked with bracket) was oxidized with sodium periodate to create new aldehydes on the IgG sugar moieties on the Fc region. This oxidized glycoprotein was reacted via reductive amination with reactive hydrazide heparosan polysaccharide using sodium cyanoborohydride. For preparation of reactive heparosan, a short heparosan tetrasaccharide acceptor (derived from nitrous acid as described earlier) was first treated with adipic dihydrazide (a compound with 2 terminal hydrazide functional groups; one end couples with sugar and the other end remains free for reaction with cargo) and then extended into a longer ~20 kDa polymer with PmHS1 enzyme and UDP-sugars. As seen by the SDS-PAGE gel visualized by autoradiography, higher molecular weight products were observed in the 'Hep' lane, corresponding to HEPylated IgG molecules (see arrow area) (unmodified IgG starting material is lane '0'; note that IgG preparations from serum contain multiple species due to the variety of heavy and light chains and there is also a small amount of higher molecular weight contaminant). This data demonstrates yet another chemistry for coupling heparosan vehicle to a therapeutic cargo such as a glycoprotein like an antibody.

Figure 10:
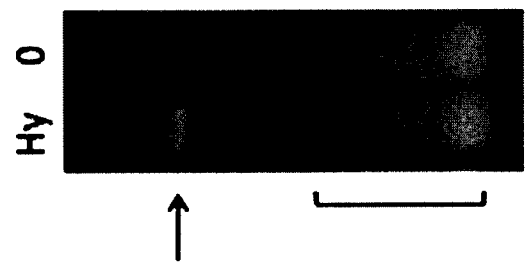
FIG. 10 is a pictorial representation of a PAGE gel visualized by virtue of ultraviolet-induced fluorescence, demonstrating production of HEPylated fluorescein molecules (see arrow). Unreacted FITC (fluorescein isothiocyanate) is bracketed.

FIG. 10 illustrates the production of HEPylated fluorescein molecules. To produce these molecules, a preparation of reactive hydrazide 75 kDa heparosan (similar reagent as in FIG. 9) was reacted with fluorescein isothiocyanate (FITC). As a control, heparosan without the reactive hydrazide group was also treated with the same FITC reagent (lane '0'). As seen by the PAGE gel visualized by virtue of ultraviolet-induced fluorescence, a higher molecular weight fluorescent product was observed in the 'Hy' lane, corresponding to HEPylated fluorescein molecules (see arrow) (unreacted FITC starting material is bracketed). This data demonstrates yet another example of coupling heparosan vehicle to a small molecule that is a proxy for a therapeutic cargo. In this case, the hydrazide linkage is meta-stable at physiological pH thus the HEPylated cargo will break down over time, facilitating time-release delivery of free small molecule. In the case of certain toxic therapeutics such as cancer chemotherapy drugs, this is a useful dosing feature.

Figure 11:
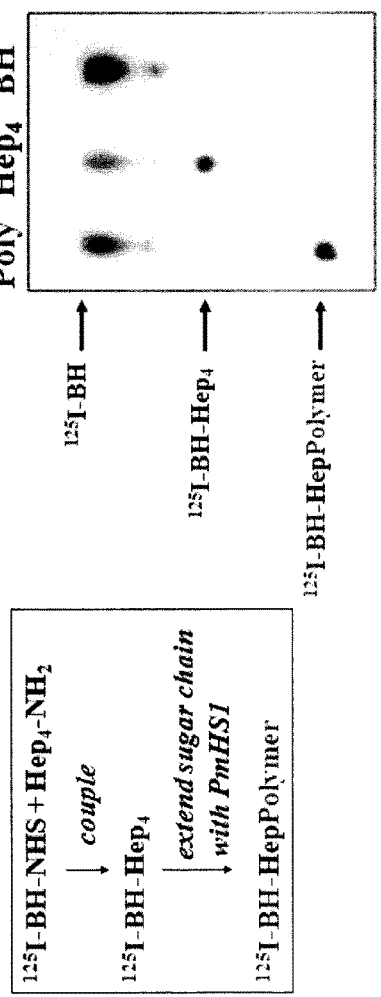
FIG. 11 is a graphical representation of thin layer chromatography (TLC) of short heparosan acceptor coupled to a radioactive cargo and its subsequent elongated product. This TLC shows the new radioactive acceptor formed by coupling BH and amino-Hep4 (middle lane) and its subsequent elongation by polymer grafting with PmHS1 synthase into a heparosan vehicle (left lane) suitable for prolonging residence time in the mammalian blood stream. (BH=$^{125}$I Bolton-Hunter reagent; Hep4=heparosan tetrasaccharide; Poly=BH conjugate of heparosan polymer of approximately 220 kDa).
Figure 12:
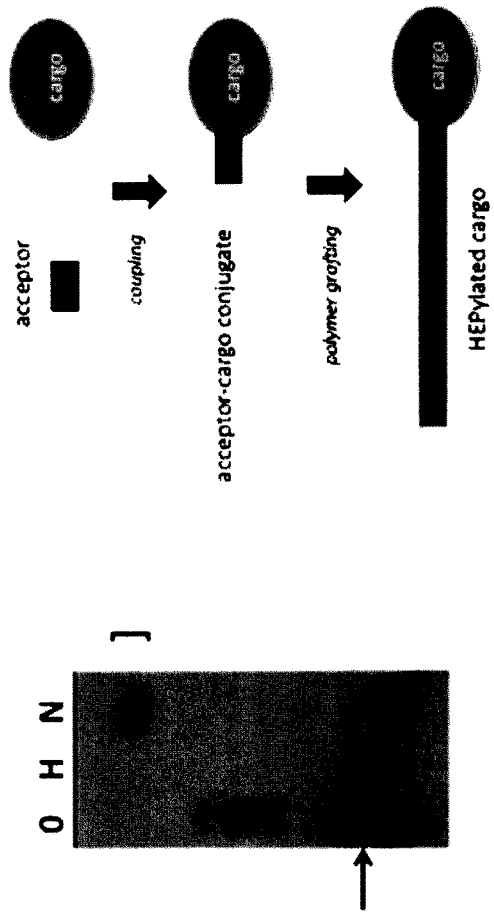
FIG. 12 is a graphic depiction (right panel) of the production of HEPylated cargo by polymer grafting, and a pictorial representation (left panel) of an SDS-PAGE gel that demonstrates the use of said method to produce HEPylated BSA molecules (see bracket area).

Alternatively, the cargo can first be coupled to the reactive acceptor, and then the heparosan chain added by polymer grafting with PmHS1 (e.g., elongate the acceptor while coupled to cargo) due to the mild reaction conditions as shown in the example of FIG. 11. In FIG. 12, radioactive bovine serum albumin ($^{125}$I-Bolton-Hunter labeled BSA) protein was reacted via reductive amination with sodium cyanoborohydride with two different reactive oligosaccharide acceptors derived from heparosan (same acceptors as in FIG. 7). For H, a heparosan tetrasaccharide formed by HCl cleavage with general structure [GlcUA-GlcNAc]$_2$ was used while for N, a heparosan tetrasaccharide formed by base treatment followed by nitrous acid cleavage with general structure [GlcUA-GlcNAc]-GlcUA-anhydromannitol was used. Then the short oligosaccharide acceptor covalently attached onto the BSA was extended via polymer grafting into a longer heparosan polymer with PmHS1 enzyme and UDP-sugars. As seen by the SDS-PAGE gel visualized by autoradiography on the left, higher molecular weight products were observed in the N lane corresponding to HEPylated BSA molecules (see bracketed area; the unmodified BSA starting material is lane '0' and is marked with arrow).

Therefore two different strategies can be used to add the heparosan vehicle onto the therapeutic cargo: (I) a long reactive polymer is directly added to the cargo as shown in the schematic model of FIG. 6 and the data in FIG. 7 or (II) a short reactive acceptor is directly added to the cargo and then this conjugated molecule is elongated via polymer grafting with PmHS1 and UDP-sugars as in FIG. 12 (data shown here on the left and schematic model on the right).

Figure 13:
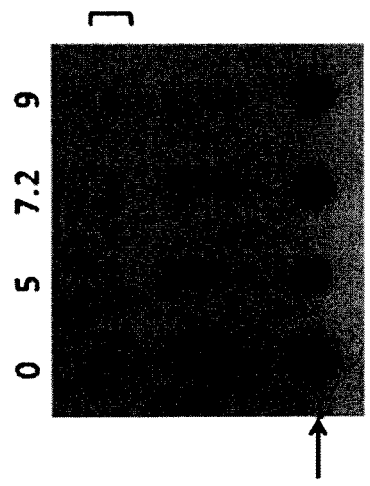
FIG. 13 is a pictorial representation of an SDS-PAGE gel demonstrating the production of HEPylated BSA molecules (see bracket area) utilizing naturally occurring heparosan obtained from in vivo microbial fermentation as the source of the vehicle.

In another example, heparosan produced by bacteria in vivo can be purified and (a) coupled via its reducing end aldehyde or (b) activated to couple to cargo (this latter approach with fermentation-derived heparosan results in functional, but more heterogeneous final products with higher polydispersity). In FIG. 13, radioactive bovine serum albumin ($^{125}$I-Bolton-Hunter labeled BSA; migration marked with arrow; lane 0=no treatment; note that some contaminating minor bands are also present in all lanes) protein was reacted via reductive amination with sodium cyanoborohydride with periodate-oxidized reactive (contains new aldehyde groups) ~200 kDa heparosan polysaccharide formed by fermentation of *Pasteurella multocida* Type F bacteria in vivo. Several reaction pHs from pH 5-9 were tested. As seen by the SDS-PAGE gel visualized by autoradiography, higher molecular weight product was observed in the reaction lanes (pH 5, 7.2, or 9) corresponding to HEPylated BSA molecules (see bracketed area). Therefore, in addition to chemoenzymatic synthetically derived heparosan vehicles, naturally occurring heparosan from microbes may also be used as the source of vehicle. Such polymers include, but are not limited to, recombinant microbial hosts (e.g., *Escherichia, Bacillus*) with heparosan synthases such as PmHS1 or other native microbes that produce heparosan such as *Escherichia coli* K5.

In order to monitor the half-life ($t_{1/2}$) and persistence of heparosan in a mouse or rat model, radioactive probes have been employed; however, ELISA or NMR may also be used to monitor the cargo. Typical elongation reactions contain: 50 mM Tris, pH 7.2, 1 mM MnCl$_2$, 1 to 50 mM UDP-sugars, 0.1 mg/ml PmHS1 enzyme and a primer; the stoichiometric ratio of primer to UDP-sugars controls the heparosan chain size.

Figure 14:
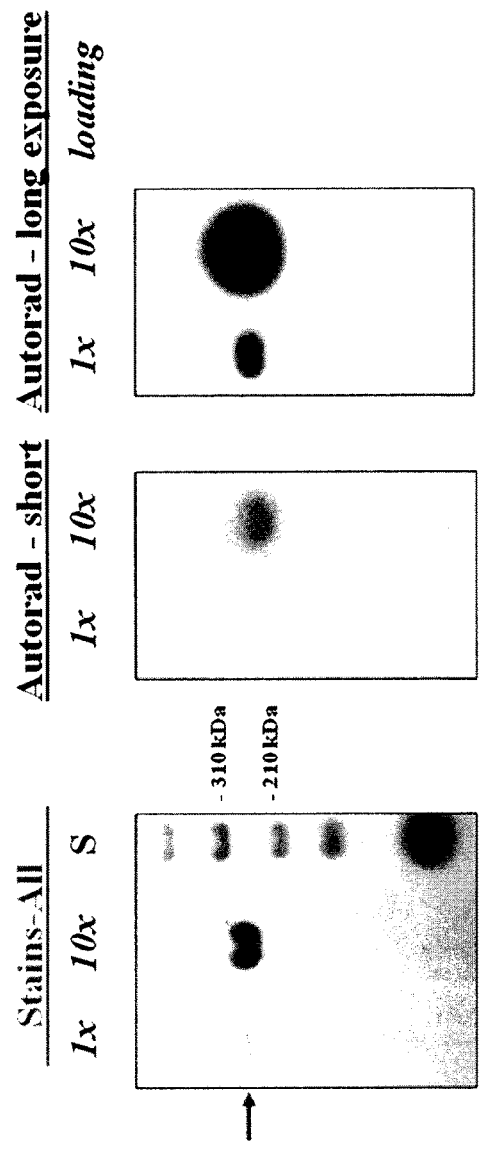
FIG. 14 is a graphical representation of an agarose gel analysis of heparosan coupled to radioactive cargo. This gel was stained with a sugar detection reagent (Stains-all) as well as exposed to X-ray film (Autorad; 2 exposure times—short or long) to illustrate the defined synthesis of a radioactive cargo coupled to approximately 220 kDa heparosan (same polymer as in the TLC of FIG. 11). The narrow size distribution (monodispersity) is demonstrated by loading of both a low (1×) and a high (10×) concentration of HEPylated probe as well as overexposure of the X-ray film.

$^{125}$I-Heparosan:

A heparosan oligosaccharide primer with a $^{125}$I-Bolton-Hunter reagent (a proxy for the therapeutic cargo) was elongated to any desired length with the PmHS1 enzyme. A series of polymers having distinct sizes, but equal radiochemical specific activity (approximately 70 Ci/mmol) were generated; an example of one such radioactive conjugate is depicted in FIG. 14. The radioactive tetrasaccharide primer was made from heparosan polysaccharide by partial de-acetylation in base, nitrous acid cleavage, reductive amination with ammonia, then coupling to NHS ester of $^{125}$I-Bolton-Hunter reagent (Perkin Elmer NEN). The strong gamma-rays were readily detectable in samples of blood or tissues without additional processing. A series of $^{125}$I-heparosan probes were created to monitor the activity and functionality of the heparosan conjugate. Here, the rat was used as the model to track the fate of the heparosan conjugate after injection, but other mammals such as man are expected to behave similarly.

Figure 3:
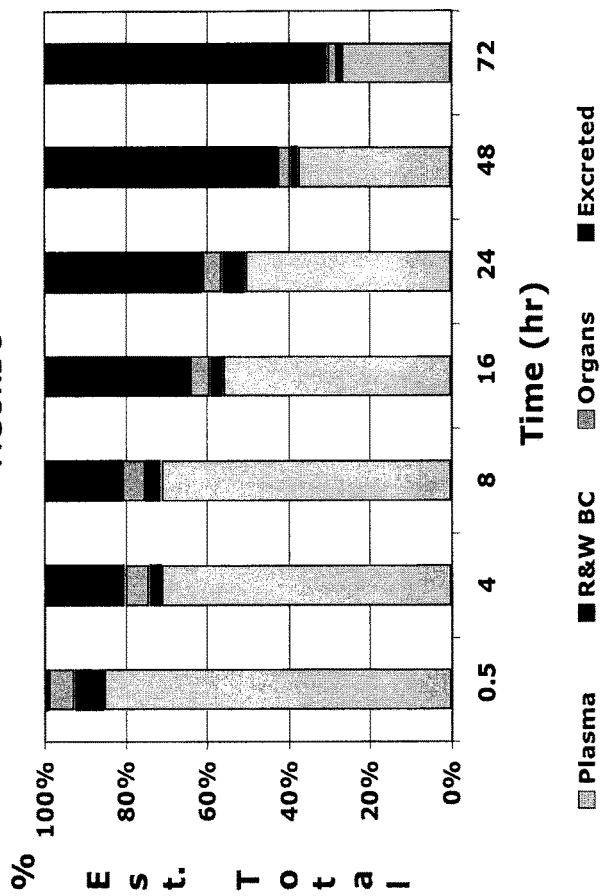
FIG. 3 is a graphical representation of the fate of a radioactive heparosan conjugate in a rat model. Rats were injected intravenously with 100 kDa $^{125}$I-heparosan polymer at 'Time 0', and at various times, the radioactivity in blood (Plasma or red and white blood cells, 'R&W BC'), organs (liver, kidney, spleen, heart, bladder, brain), and excreted waste (urine, feces) was measured. The data indicate that heparosan, the active molecule of HEPylation, circulated in the plasma of the mammalian blood stream, did not accumulate in major organs (note: the low signal present is due to blood trapped in organs based on saline-perfused controls), and was excreted via normal pathways (i.e., urine, feces).

Three commonly employed modes of a therapeutic injection were tested: (a) intravenous (i.v.); (b) intraperitoneal (i.p.) and (c) intramuscular (i.m.). On the order of 5-50 uCi (approximately $10-100 \times 10^6$ dpm) radioactive heparosan probe in a small volume of saline per mouse or rat was injected at time zero into the tail vein or an implanted jugular port (i.v.) or abdominal cavity (i.p.) or the rear flank (i.m.). A group of animals was injected in parallel. The mice or rats were kept in special cages to facilitate urine and feces collection. At various times (typically 5, 30, 60, 120, minutes and 1 to 5 days), blood was drawn from the animals. Duplicate animals were used for each time point. Some animals were sacrificed at early time points for harvesting organs that are known for potentially interacting with injected therapeutics (e.g., the kidney and the liver). The fate of injected heparosan conjugate in the mammalian body is shown in the example of FIG. 3.

For $^{125}$I-probes, the samples (equal volumes or weights per sample) were placed directly in test tubes and measured with a solid-state gamma scintillation counter for 1 minute. For detecting low amounts of radioactivity, the counting interval was extended to 5 or 10 minutes per sample (with a comparable blank value subtracted). The amount of radioactivity in the various samples overtime was used to calculate half-life in various compartments. Longer chains of heparosan and heparosan conjugates persist in blood after i.v. injection for long periods of time. Heparosan and heparosan conjugates percolate slowly out of the abdomen after i.p. injection, and thereafter appear in the blood. Heparosan and heparosan conjugates percolate slowly out of the muscle after i.m. injection and thereafter appear in the blood.

Materials and Methods

Animals:

Experiments were performed on male Sprague-Dawley rats (270-345 g at time of experiment) purchased from Charles River (Wilmington, Mass.) with a polyurethane catheter implanted into the right jugular vein. Rats were housed under controlled conditions (25° C., 12 h light/dark cycle) with free access to food and water. Upon arrival, each rat was placed into a cage and acclimated to the animal facility for at least 7 days. The Institutional Animal Care and Use Committee of Oklahoma University Health Sciences Center approved the animal use for this protocol (#08-082R).

Test Compounds:

The two test compounds (FIG. 2A—100 kDa or FIG. 2B—60 kDa polymer) were constructed in a radiolabeled form with I-125 (70 Ci/mmol) as described previously. The activity of the radiolabel was set at 0.94 μCi per 0.2 ml. The use of I-125 for this study was reviewed and approved by the OUHSC Radiation Safety Office.

Dosing:

Rats were anesthetized by isoflurane inhalation (5-2% to effect) before being administered 0.2 ml of the radiolabeled test compound by i.v. infusion into the right jugular vein. Following compound infusion, the i.v. catheter was flushed with 0.2 ml of sterile saline and then the catheter was locked with 0.2 ml of sterile heparinized saline (1% v/v, 10 U/ml). Rats were then placed into holding cages until being reanesthetized just before a terminal blood draw and organ collection.

The following groups of rats were dosed:

FIG. 2A—100 kDa

| Group 1: | 0.5 hr post-dosing | n = 2 rats |
| Group 2: | 4 hr post-dosing | n = 2 rats |
| Group 3: | 8 hr post-dosing | n = 2 rats |
| Group 4: | 16 hr post-dosing | n = 2 rats |
| Group 5: | 24 hr post-dosing | n = 2 rats |
| Group 6: | 48 hr post-dosing | n = 2 rats |
| Group 7: | 72 hr post-dosing | n = 2 rats |

FIG. 2B—60 kDa

| Group 1: | 0.5 hr post-dosing | n = 2 rats |
| Group 2: | 4 hr post-dosing | n = 2 rats |
| Group 3: | 8 hr post-dosing | n = 2 rats |
| Group 4: | 16 hr post-dosing | n = 2 rats |
| Group 5: | 24 hr post-dosing | n = 2 rats |
| Group 6: | 30 hr post-dosing | n = 2 rats |
| Group 7: | 48 hr post-dosing | n = 2 rats |

Perfusion Groups

| Group 1: | Probe 1, 24 hr post-dosing | n = 3 rats |
| Group 2: | Probe 2, 16 hr post-dosing | n = 3 rats |

Sampling and Counting:

At the post-dosing time-points listed above rats were euthanized via a terminal blood draw while under isoflurane anesthesia. Blood was drawn using a 10 cc syringe connected to the i.v. catheter. Median blood volume withdrawn was 10 ml (3 ml, min—11.5 ml, max). For the perfusion groups, 1.5-3.8 ml of blood was withdrawn before perfusion. Blood was then transferred into 15 ml Falcon tubes and centrifuged (3000 rpm for 15 min. at 4° C., Beckman tabletop centrifuge) to separate plasma from blood cells. Once separated, 0.1 ml each of plasma and blood cells were transferred into plastic culture tubes for subsequent determination of radioactivity. In addition, liver (3 tubes), spleen (1 tube), kidneys (1 tube/kidney), bladder (empty—1 tube), heart (1 tube), lungs (1 tube/lung), brain (perfusion groups only—2 tubes) and any urine (1 tube) or fresh fecal pellets (1 tube) were collected and prepared for radioactive counting. To determine blood plasma half-life and relative distribution of the test compound, the samples were placed into a gamma counter were the total radioactivity was converted into counts per minute (CPM). Similar studies were done for i.m. and i.p. injection.

Transcardial Perfusion:

At the post-dosing time-points listed above, following blood withdrawal under isoflurane anesthesia, rats were euthanized via cardiac perfusion with 200 ml of ice-cold sterile saline. For the perfusion, anesthetized rats were placed on a wire mesh cage top over a sink. Their fore limbs were then taped to the cage top so that the chest cavity was exposed. Using forceps to stabilize the skin, an initial cut with scissors was used to expose the musculature of the chest and upper abdomen. The caudal tip of the sternum was then grasped, and the diaphragm was rapidly punctured with the scissors, followed by cutting through the sternum to expose the heart. Additional cuts to the ribs were made with hemostats applied to act as retractors to provide an unobstructed view of the heart. The perfusion system consisted of a peristaltic pump (Masterflex, Cole-Parmer, Vernon Hills, Ill.) used at a setting of '7' with tubing connected to a 16 gauge needle that was inserted into the left ventricle of the heart which was gently held in place with forceps to deliver ice-cold sterile saline. The right atrium was then cut to allow the blood and saline to exit the circulatory system. The quality of the perfusion was dependent on the amount of time the heart remained beating following insertion of the perfusion needle and could be monitored by the loss of color from the tail, hind limbs and liver. At the end of the perfusion, the rat had its organs removed and counted as previously listed.

Data Analysis:

pK values: The blood plasma half-life ($T_{1/2}$ or K10) of the test compound was determined with WinNonLin software (version 5.2.1) using a Gauss-Newton modeling algorithm (#7), as shown below. Additional derived pK values including the area under the curve, Cmax, and body clearance were calculated by the same software package.

Calculation of total activity: Total activity was determined at each time point based on the averaged activity for each listed sample based on the following calculations:

Estimated total blood volume=[rat body weight (g)/100]×6 ml

Plasma ratio=ml of plasma/ml of total blood withdrawn

Platelet ratio=ml of blood cells/ml of total blood withdrawn

Estimated total plasma volume=plasma ratio×est. total blood volume

Estimated total blood cell volume=platelet ratio×est. total blood volume

Total plasma CPM=plasma CPM/100 μl×1000 μl/1 ml×est. total plasma volume

Total blood cell CPM=blood cell CPM/100 μl×1000 μl/1 ml×est. total blood cell volume Total organ CPM=liver CPM+spleen CPM+kidney CPM+bladder CPM+heart CPM+lung CPM Total Activity=total plasma+total blood cells+total organ 0.5 hr Excreted CPM=0.5 hr urine CPM+0.5 hr fecal CPM Maximum Activity=0.5 hr Total Activity+0.5 hr
Excreted CPM % Recovery=Total Activity/Maximum Activity Excreted CPM (all other time points)=Maximum
Activity−Total Activity Calculation of % Relative Activity: For each time-point, the average activity for the sample (plasma, blood cells or individual organ) was divided by the Total Activity for that time-point. Thus, the total of all the Relative Activity=100% for each time-point, but the Total Activity always decreased as the probe was excreted.

Calculation of Perfusion Correction Factor: Data following perfusion from individual animals was compared to the values obtained from non-perfused animals at the same time-point. The average activity for each organ was expressed as a percentage of the non-perfused activity of the same organ—this percentage was then used as the Perfusion Correction Factor and was applied to all time points for the same organ to determine a Corrected % Relative Activity (% relative activity×perfusion correction factor=perfusion corrected % relative activity). For both probes, following application of the correction factor, the activity that was removed from the organs was added to the % relative activity for the plasma and blood cells to keep the total at 100% per time-point.

Figure 2A:
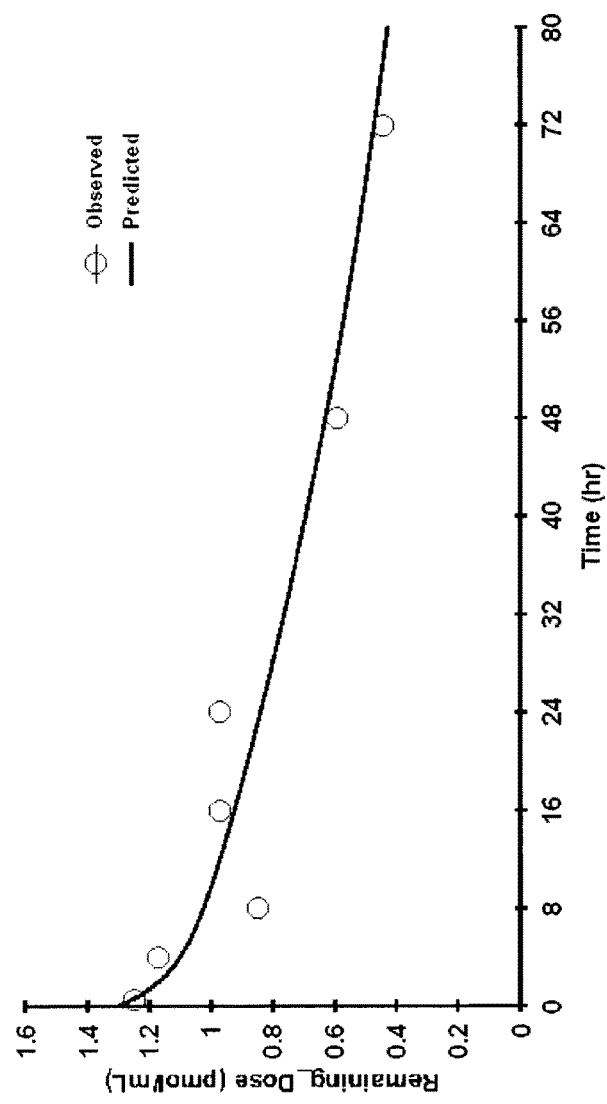
FIG. 2A is a graphical representation of the pharmacokinetics (pK) of radioactive heparosan conjugate in plasma in a rat model. Rats were injected intravenously with $^{125}$I-heparosan polymer (100 kDa mass) at 'Time 0', and at various times, blood was drawn, and the radioactivity in the plasma was measured. The data indicate that 100 kDa heparosan, the active molecule of HEPylation, has a long lifetime (half-life of approximately 2 days) in the mammalian bloodstream.
Figure 2B:
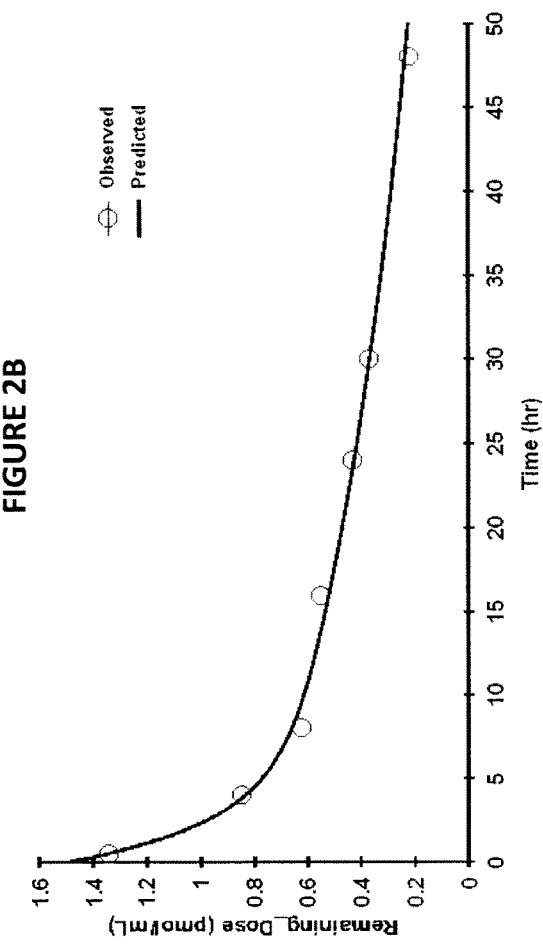
FIG. 2B is a graphical representation of the pharmacokinetics of radioactive heparosan conjugate in plasma in a rat model. Rats were injected intravenously with $^{125}$I-heparosan polymer (60 kDa monodisperse polymer) at 'Time 0', and at various times, blood was drawn, and the radioactivity in the plasma was measured. The data indicate that 60 kDa heparosan, the active molecule of HEPylation, has a long lifetime (half-life of approximately 15 hours) in the mammalian bloodstream. In addition, upon comparison of the data in FIGS. 2A and 2B, the size of the polymer determines the plasma half-life, thus allowing tuning of drug-conjugate pharmacokinetics.

Pharmacokinetics (pK) Results pK analysis Probe 1: FIG. 2A shows the curve-fit for the elimination of the radioactivity from the plasma for Probe 1. From the software analysis of the data, the $T_{1/2}$ (half-life) or the elimination constant was 49.8 hours. The area under the curve (AUC) was 93.3 (hr)(pmol/ml) with a Cmax of 1.30 pmol/ml and a clearance of 0.014 ml/hr.

pK analysis Probe 2: FIG. 2B shows the curve-fit for the elimination of the radioactivity from the plasma for Probe 2. From the software analysis of the data, the $T_{1/2}$ for the elimination constant was 15.4 hours. The area under the curve was 33.0 (hr)(pmol/ml) with a Cmax of 1.48 pmol/ml and a clearance of 0.040 ml/hr. In addition to long plasma half-life, the heparosan molecular weight is stable in the mammalian bloodstream as shown in FIG. 4.

Figure 15:
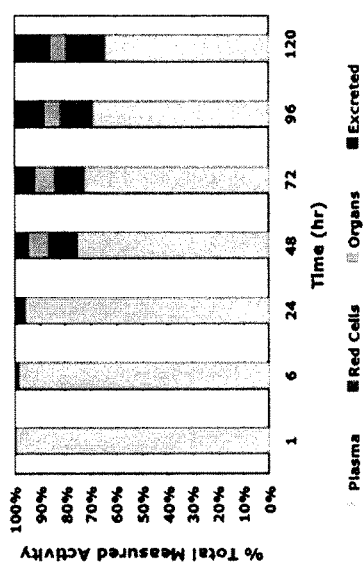
FIG. 15 is a graphical representation of the total distribution of the measured radioactivity from FIG. 16 for i.m. dosing.

FIG. 15 depicts an analysis of the blood plasma half-life and the blood absorption half-life of a radioactive heparosan compound following injection thereof into rats. Male Sprague-Dawley rats received two 0.1 ml injections of the radioactive heparosan compound (i.m.) in both hind limb calves. This test compound (100 kDa) was radiolabeled with $^{125}$I (70 Ci/mmol). The activity of the radiolabel was set at 4.0 µCi per 0.2 ml, however testing demonstrated that 10% of the probe was retained within the syringes, thus the effective dose was 3.6 µCi. At 1, 6, or 24 hr post-injection, 0.5 ml of whole blood was collected from the tail vein, while at 48, 72, 96 or 120 hr post-injection the rats were euthanized with blood and organs collected to determine distribution of the probe. The blood plasma half-life ($T_{1/2}$ or K10) and the blood absorption half-life (K01) of the test compound was determined with WinNonLin software (version 5.2.1) using a Gauss-Newton modeling algorithm.

FIG. 15 shows the total distribution of the measured radioactivity for i.m. dosing. As shown, the majority of the activity remains in the plasma with relatively constant activity in the red cells and organs. The amount of radioactivity in the different organs dissected from the rats was also measured. The activity in the liver was less than 3.0% of total activity at all time points. Total activity in the spleen was always less than 0.3%. This data indicates that i.m. dosing does not accumulate in these organs. Activity in the kidneys from remained about 2% of the total activity. Activity in the bladder was minimal (<0.2%) at all time points. The probe did not accumulate in either the heart or the lungs as activity in both organs was 1% or less throughout the study. Based on the perfusion tests where residual blood was washed out of organs, this small amount of radioactivity was due to trapped blood (for i.m. and i.p. studies, no perfusion was performed). Finally, while the injection site muscle already had a low % total activity (<2%) at the first measured time point, the activity further decrease to less than 1% by the end of the experiment. At all time-points when samples were available, both the urine and the fecal pellets were radioactive, demonstrating that with i.m. dosing excretion began by 6 hr post-dosing and continued throughout the testing period. This radioactivity is due to the residual Bolton-Hunter group attached to a small sugar chain (less than 4 units). Finally, at 96 hr, the brain accounted for 0.2% of the total activity and the testis had 0.3% of the total activity for that rat.

Figure 16:
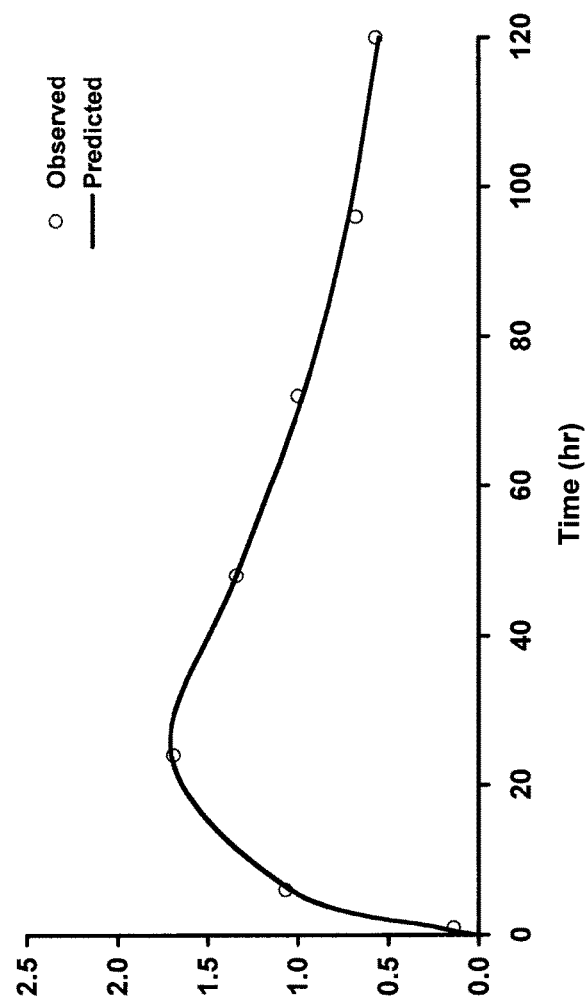
FIG. 16 is a graphical representation illustrating the curve-fit for pK analysis of the elimination of a radioactive heparosan compound from the plasma for i.m. dosing.

FIG. 16 shows the curve-fit for the elimination of the radioactivity from the plasma for i.m. dosing. From the software analysis of the data, the $T_{1/2}$ for the absorption constant was 6.8 hours and the $T_{1/2}$ for the elimination constant was 64.8 hours. The area under the curve was 224.3 (hr)(pmol/ml) with a Cmax of 1.70 pmol/ml (33.6% of total dose) at 21.9 hr and a clearance of 0.022 ml/hr.

In addition to intravenous and intramuscular injection, radioactive heparosan was administered to animals via an abdominal injection. Male Sprague-Dawley rats received a single 0.2 ml injection of the 100 kDa heparosan (i.p.) into the peritoneum. At 1, 6, or 24 hr post-injection, 0.5 ml of whole blood was collected from the tail vein, while at 48, 72, 96 or 120 hr post-injection the rats were euthanized with blood and organs collected to determine distribution of the probe in a similar to the i.m. study.

Similar to the i.m. dosing study, the $T_{1/2}$ was at least 2 days when heparosan was injected i.p. The activity in the liver was less than 3% all time-points. Similar to the i.m. dosing, total activity in the spleen was always less than 0.3%. The activity in the kidneys was 2% or less at all time-points. Activity in the bladder was minimal (<0.1%). The probe did not accumulate in either the heart or the lungs. This data indicates that i.p. dosing does not accumulate in these organs. At all time-points with measurements, both the urine and the fecal pellets were radioactive, demonstrating that i.p. dosing excretion began within the first hour post-dosing and continued throughout the testing period.

Figure 17:
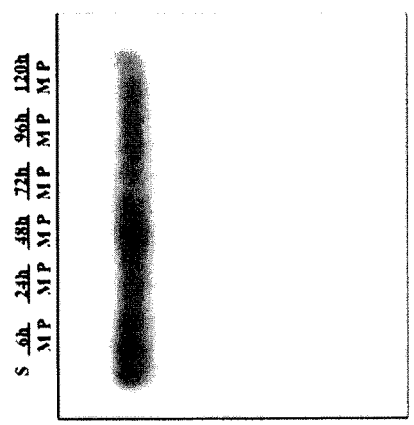
FIG. 17 is a pictorial representation of an agarose gel demonstrating the stability of the heparosan vehicle utilized in FIGS. 15-16 in the extracellular compartments of the mammalian body.

If the heparosan is not degraded in the extracellular compartments of the mammalian body and thus possesses stability, then the chain length or molecular weight should remain unchanged. The molecular weight of the heparosan samples from the of i.m. Study (M lanes) that generated the plot of FIG. 15 as well as the samples from i.p. (P lanes) study was examined by gel electrophoresis, as shown in FIG. 17. Basically, equal amounts of radioactivity in the plasma from various time points were concentrated into a small volume by ultrafiltration (Micron 10 kDa cut-off). The samples were loaded on an 1×TAE agarose gel (as in FIG. 4), electrophoresed, dried and exposed to X-ray film. As a control, the original starting radioactive heparosan (100 kDa) was also loaded (lane S). The data show that the heparosan migrates from the injection site through the various tissues and compartments and gets into blood stream in an intact form with the same molecular weight as the starting polymer. Even after 5 days (120 hours), the heparosan vehicle remains intact thus indicating its suitability as a useful vehicle for enhancing therapeutics.

Analyses of Metabolites after Leaving Bloodstream

Figure 18:
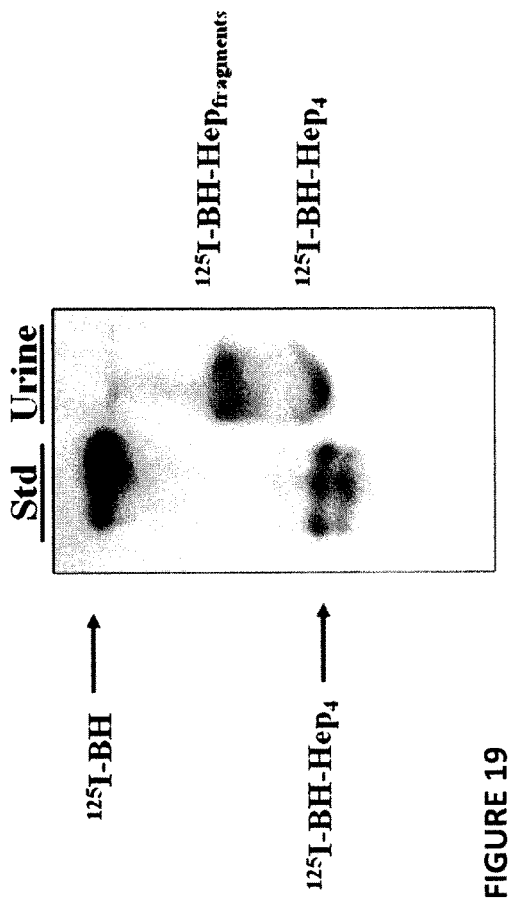
FIG. 18 is a graphical representation of TLC of Urine Metabolites. A radioactive conjugate of approximately 220 kDa heparosan/Bolton-Hunter reagent was injected into a rat. After 2 days, the radioactive breakdown products excreted into urine were analyzed by TLC (similar to FIG. 11). Small size fragments (equal or less than 4 sugar units or n=2) of the original probe are observed, indicating metabolic breakdown of the natural heparosan polymer after leaving the bloodstream (note: this approximately 220 kDa conjugate before injection into the rat would remain at the origin of the TLC plate as in FIG. 11 and not run up the TLC plate as shown here).

Urine: Urine from various time points was extracted with chloroform to remove proteins and concentrated by ultrafiltration as above; the vast majority of the radioactivity passed through the 3 kDa membranes thus the heparosan fragments that passed through the kidneys was smaller than 3 kDa. This material was then subjected to thin layer chromatography (TLC) on silica plates developed with butanol:acetic acid:water solvent. The plate was then exposed to X-ray film; only small metabolized fragments (4 sugar units and less or n=2 or less) of the original heparosan were observed as shown in FIG. 18.

Figure 19:
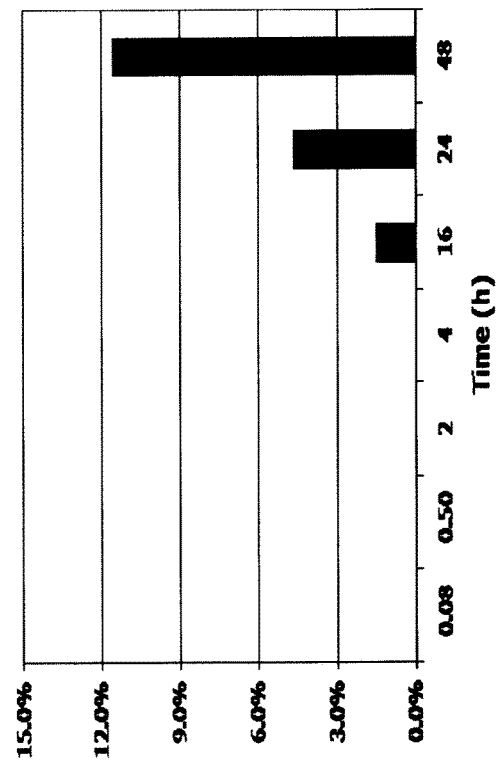
FIG. 19 is a graphical representation of heparosan metabolite excretion into feces. A conjugate of approximately 220 kDa heparosan/Bolton-Hunter was injected into a rat. Over 2 days time, the radioactive breakdown products excreted into feces were measured in a gamma counter and plotted here as the percent fraction of the entire initial dose. Excretion into feces and urine accounts for the metabolized heparosan vehicle indicating that heparosan does not accumulate in a mammalian patient (as shown in FIG. 3). The size of the radioactive polymers in the feces was less than 3 kDa (or less than 15 sugar units) as measured by ultrafiltration, thereby indicating that heparosan is degraded and then excreted over time.

Feces: After injection into rats, heparosan metabolites were excreted in feces over time as shown in FIG. 19. Water extracts of feces from various time points after injection were subjected to ultrafiltration with various molecular weight cut-off membranes (3, 10, or 50 kDa; Amicon Microcon) and gamma counting of the retained and eluted fractions. The size of the radioactive metabolites were inferred by the ability to penetrate the pores of the membrane; the vast majority of the radioactivity passed through the 3 kDa membranes; thus, the heparosan fragments that passed through the intestines was smaller than 3 kDa.

Reductive Amination Drug-Conjugate Synthesis

The aldehyde of heparosan polymers (e.g., either the natural reducing end or via periodate oxidation) is coupled directly to therapeutic proteins via its N-terminal amino groups using reductive amination with Na cyanoborohydride. For adding a single heparosan polymer per polypeptide chain, the reaction is done in 0.1 M Na acetate, pH 5, at 4° to 37° C.; the buffer pH used de-selects the lysine groups with higher pKa (need an unprotonated amine for nucleophilic attack) in favor of the amino terminus. Lower temperatures (e.g. 4° to 10° C.) is used to preserve protein folding. Alternatively, reactions at pH 7-9 (e.g., in phosphate buffer) are used to add multiple heparosan chains to the lysines as well as the N-terminus of the protein cargo. This methodology is therapeutically and commercially successful for proteins like interferons and GCSF (Neulasta). A wide variety of chemistries are useful for successful conjugate synthesis; the basic requirements are (a) there is an appropriate reactive or activated group on the heparosan polymer vehicle (either short acceptor or longer polymers) that will react or interact with a group on the cargo (i.e., therapeutic agent or drug), or if desired, a secondary vehicle (e.g., liposome or nanoparticle), and (b) suitable mild reaction conditions that preserve the integrity and functionality of both the vehicle and the cargo.

Thus, in accordance with the presently disclosed and claimed invention(s), there has been provided a methodology for HEPylation wherein a heparosan molecule servers as the vehicle for carrying a cargo in a heparosan-conjugate. Although the presently claimed and disclosed invention(s) has been described in conjunction with the specific drawings and language set forth above, it is evident that many alternatives, modifications and variations will be apparent to those skilled in the art. Accordingly, it is intended to embrace all such alternatives, modifications and variations that fall within the spirit and broad scope of the invention.

What is claimed is:

1. A method for preparing a pharmaceutically active conjugate for administration to a mammalian patient, comprising the steps of:
reacting at least one therapeutic drug with at least one heparosan polymer under conditions sufficient to effect covalent conjugation of the at least one therapeutic drug and the at least one heparosan polymer to form a reaction mixture containing one or more drug-heparosan polymer conjugates, wherein the at least one therapeutic drug remains active after conjugation and does not increase immunoreactivity of the at least one heparosan polymer, and wherein the at least one therapeutic drug is an agent used in the treatment of cancer or an inflammatory condition; and
forming a sterile pharmaceutical formulation comprising the drug-heparosan polymer conjugates in a unit dosage format for therapeutic injection into the patient.

2. The method of claim 1, wherein the one or more drug-heparosan polymer conjugates comprise a therapeutic drug having a single heparosan polymer conjugated thereto.

3. The method of claim 1, wherein the at least one heparosan polymer has a mass in a range of from about 600 Da to 800 kDa.

4. The method of claim 1, wherein the at least one heparosan polymer is monodisperse.

5. The method of claim 1, wherein the at least one heparosan polymer is unsulfated and unepimerized.

6. The method of claim 1, wherein the drug-heparosan conjugate exhibits increased retention in blood circulation of a mammalian patient when compared to drug alone.

7. The method of claim 1, wherein the drug-heparosan conjugate exhibits reduced occurrence of accumulation in organs of a mammalian patient when compared to drug alone.

8. The method of claim 1, wherein the one or more drug-heparosan polymer conjugates comprise a therapeutic drug having multiple heparosan polymers conjugated thereto.

9. The method of claim 1, wherein the at least one heparosan polymer is further characterized as being substantially non-targeting.

10. The method of claim 1, further comprising the step of modifying the at least one heparosan polymer prior to reacting with the at least one therapeutic drug to provide at least one reactive group on the at least one heparosan polymer with which a group on the at least one therapeutic drug reacts to effect the covalent conjugation of the at least one therapeutic drug to the at least one heparosan polymer.

11. The method of claim 10, wherein the at least one reactive group is selected from the group consisting of an aldehyde, alkyne, ketone, maleimide, thiol, azide, amino, hydrazide, phosphate, sulfate, nitrate, carbonate, ester, chelator, and combinations thereof.

12. The method of claim 10, wherein the step of modifying the at least one heparosan polymer is further defined as creating at least one amine-, carbonyl-, and/or sulfhydryl-reactive group on the at least one heparosan polymer.

13. The method of claim 1, wherein the at least one therapeutic drug is selected from a therapeutic peptide, polypeptide, or protein.

14. The method of claim 1, wherein the at least one heparosan polymer is further characterized as having a multi-hour half-life within extracellular compartments of the mammalian patient.

15. The method of claim 14, wherein the at least one heparosan polymer has a half-life of at least 15 hours within extracellular compartments of the mammalian patient.

16. A method for preparing a pharmaceutically active conjugate for administration to a mammalian patient, comprising the steps of:
modifying at least one heparosan polymer to provide at least one reactive group on the at least one heparosan polymer that is available to form a bond to a therapeutic drug;
reacting at least one therapeutic drug with the at least one modified heparosan polymer under conditions sufficient for the at least one reactive group on the at least one modified heparosan polymer to react with a group on the at least one therapeutic drug and thereby effect covalent conjugation of the at least one therapeutic drug and the at least one heparosan polymer, thereby forming a reaction mixture containing one or more drug-heparosan polymer conjugates, wherein the at least one therapeutic drug remains active after conjugation and does not increase immunoreactivity of the at least one heparosan polymer, and wherein the at least one therapeutic drug is an agent used in the treatment of cancer or an inflammatory condition; and
forming a sterile pharmaceutical formulation comprising the drug-heparosan polymer conjugates in a unit dosage format for therapeutic injection into the patient.

17. A method for preparing a pharmaceutically active conjugate for administration to a mammalian patient, comprising the steps of:
reacting at least one therapeutic drug with at least one heparosan polymer under conditions sufficient to effect covalent conjugation of the at least one therapeutic drug and the at least one heparosan polymer, the at least one heparosan polymer having at least one amine-, carbonyl-, and/or sulfhydryl-reactive group that reacts with a group on the at least one therapeutic drug to conjugate the heparosan polymer and the at least one therapeutic drug, thereby forming a reaction mixture containing one or more drug-heparosan polymer conjugates, wherein the at least one therapeutic drug remains active after conjugation and is not an adjuvant, and wherein the at least one therapeutic drug is an agent used in the treatment of cancer or an inflammatory condition; and
forming a sterile pharmaceutical formulation comprising the drug-heparosan polymer conjugates in a unit dosage format for therapeutic injection into the patient.

18. The method of claim 1, wherein the at least one therapeutic drug is selected from the group consisting of a cytokine, a hormone, an enzyme, an antibody, an antibody fragment, and combinations thereof.

19. The method of claim 16, wherein the at least one therapeutic drug is selected from the group consisting of a cytokine, a hormone, an enzyme, an antibody, an antibody fragment, and combinations thereof.

20. The method of claim 17, wherein the at least one therapeutic drug is selected from the group consisting of a cytokine, a hormone, an enzyme, an antibody, an antibody fragment, and combinations thereof.

21. A method for preparing a pharmaceutically active conjugate for administration to a mammalian patient, comprising the step of:
forming a sterile pharmaceutical formulation comprising at least one drug-heparosan polymer conjugate in a unit dosage format for therapeutic injection into the patient, wherein the drug-heparosan polymer conjugate comprises at least one therapeutic drug covalently conjugated to at least one modified heparosan polymer, wherein the at least one heparosan polymer has been modified to provide at least one reactive group on the at least one heparosan polymer that forms a covalent bond with the at least one therapeutic drug, and wherein the at least one therapeutic drug remains active after conjugation and does not increase immunoreactivity of the at least one heparosan polymer, and wherein the at least one therapeutic drug is at least one of an anti-cancer agent or an anti-inflammatory agent.

22. The method of claim 1, wherein the therapeutic drug-heparosan polymer conjugate exhibits reduced immunogenicity when compared to therapeutic drug alone.

23. The method of claim 1, wherein the one or more drug-heparosan polymer conjugates comprises a heparosan polymer having multiple therapeutic drugs conjugated thereto.

24. The method of claim 1, wherein the at least one therapeutic drug is not an adjuvant.

25. The method of claim 21, wherein the anti-cancer agent is selected from the group consisting of cis-platin, actinomycin D, doxorubicin, vincristine, vinblastine, etoposide, amsacrine, mitoxantrone, tenipaside, taxol, colchicine, cyclosporin A, phenothiazines, thioxantheres, and combinations thereof.

26. The method of claim 21, wherein the anti-inflammatory agent is selected from the group consisting of acetaminophen, aspirin, salicylic acid, methyl salicylate, choline salicylate, glycol salicylate, 1-menthol, camphor, mefenamic acid, fluphenamic acid, indomethacin, diclofenac, alclofenac, ibuprofen, ketoprofen, naproxene, pranoprofen, fenoprofen, sulindac, fenbufen, clidanac, flurbiprofen, indoprofen, protizidic acid, fentiazac, tolmetin, tiaprofenic acid, bendazac, bufexamac, piroxicam, phenylbutazone, oxyphenbutazone, clofezone, pentazocine, mepirizole, and combinations thereof.

27. The method of claim 1, wherein the at least one therapeutic drug is an agent used in the treatment of cancer.

28. The method of claim 27, wherein the agent used in the treatment of cancer comprises Granulocyte Colony Stimulating Factor (GCSF).

29. The method of claim 1, wherein the at least one therapeutic drug is an agent used in the treatment of an inflammatory condition.

30. The method of claim 16, wherein the at least one agent used in the treatment of cancer comprises Granulocyte Colony Stimulating Factor (GCSF).

31. The method of claim 17, wherein the at least one agent used in the treatment of cancer comprises Granulocyte Colony Stimulating Factor (GCSF).

* * * * *

UNITED STATES PATENT AND TRADEMARK OFFICE
CERTIFICATE OF CORRECTION

| | | |
|---|---|---|
| PATENT NO. | : 9,687,559 B2 | Page 1 of 1 |
| APPLICATION NO. | : 12/556324 | |
| DATED | : June 27, 2017 | |
| INVENTOR(S) | : Paul L. DeAngelis | |

It is certified that error appears in the above-identified patent and that said Letters Patent is hereby corrected as shown below:

In the Specification
Column 11, Line 50: Delete "chlorocyclizine," and replace with -- chlorcyclizine, --
Column 12, Line 39: Delete "trichloromethiazide," and replace with
-- trichlormethiazide, --
Column 12, Line 58: Delete "phenyloin," and replace with -- phenytoin, --
Column 19, Line 35: After "ability of the" insert -- PmHS1 --

Signed and Sealed this
Eighth Day of August, 2017

Joseph Matal
*Performing the Functions and Duties of the*
*Under Secretary of Commerce for Intellectual Property and*
*Director of the United States Patent and Trademark Office*